(12) United States Patent
Boudreaux et al.

(10) Patent No.: US 12,076,075 B2
(45) Date of Patent: Sep. 3, 2024

(54) ELECTROSURGICAL INSTRUMENT WITH FLOATING JAW COMPONENT

(71) Applicant: Cilag GmbH International, Zug (CH)

(72) Inventors: Chad P. Boudreaux, Cincinnati, OH (US); Barry C. Worrell, Centerville, OH (US); Mark A. Davison, Maineville, OH (US)

(73) Assignee: Cilag GmbH International, Zug (CH)

( * ) Notice: Subject to any disclaimer, the term of this patent is extended or adjusted under 35 U.S.C. 154(b) by 586 days.

(21) Appl. No.: 17/371,172

(22) Filed: Jul. 9, 2021

(65) Prior Publication Data

US 2022/0008120 A1 Jan. 13, 2022

Related U.S. Application Data

(60) Provisional application No. 63/050,304, filed on Jul. 10, 2020.

(51) Int. Cl.
*A61B 18/14* (2006.01)
*A61B 18/00* (2006.01)

(52) U.S. Cl.
CPC ............ *A61B 18/1445* (2013.01); *A61B 2018/00083* (2013.01); *A61B 2018/1452* (2013.01); *A61B 2018/1467* (2013.01)

(58) Field of Classification Search
CPC ............ A61B 18/1442; A61B 18/1445; A61B 2018/00071; A61B 2018/00083; A61B 2018/00607; A61B 2018/0063; A61B 2018/1452; A61B 2018/1455; A61B 2018/1465; A61B 2018/1467; A61B 2018/1475; A61B 2018/1495; A61B 2018/1497; A61B 17/068; A61B 17/28; A61B 17/285; A61B 17/29; A61B 17/295; A61B 2017/2825; A61B 2017/2829; A61B 2017/2919; A61B 2017/2926; A61B 2017/2931; A61B 2017/2933; A61B 2017/2937; A61B 2017/2939; A61B 2017/2945

See application file for complete search history.

(56) References Cited

U.S. PATENT DOCUMENTS 5,833,697 A * 11/1998 Ludwick .............. A61B 17/062
606/147
6,500,176 B1 12/2002 Truckai et al.
(Continued)

*Primary Examiner* — Robert A Lynch
(74) *Attorney, Agent, or Firm* — Frost Brown Todd LLP

(57) ABSTRACT

An apparatus includes a shaft assembly and an end effector, which includes first and second jaws pivotably coupled together. The first jaw includes a first jaw body and a first electrode surface. The second jaw includes a second jaw body and an electrode assembly, which includes a distal end pivotably supported by the distal end of the second jaw body. The electrode assembly further includes a second electrode surface positioned to face the first electrode surface when the first and second jaws are placed in a closed configuration. The first and second electrode surfaces are operable to apply RF energy to tissue. The electrode assembly further includes at least one compressible member interposed between the second electrode surface and the second jaw body. The at least one compressible is being configured to urge a proximal region of the second electrode surface toward a corresponding region of the first electrode surface.

20 Claims, 15 Drawing Sheets

(56) References Cited

U.S. PATENT DOCUMENTS

| | | | |
|---|---|---|---|
| 6,783,524 | B2 | 8/2004 | Anderson et al. |
| 8,888,809 | B2 | 11/2014 | Davison et al. |
| 8,939,974 | B2 | 1/2015 | Boudreaux et al. |
| 8,986,302 | B2 | 3/2015 | Aldridge et al. |
| 9,149,325 | B2 | 10/2015 | Worrell et al. |
| 9,161,803 | B2 | 10/2015 | Yates et al. |
| 9,526,565 | B2 | 12/2016 | Strobl |
| 9,545,253 | B2 | 1/2017 | Worrell et al. |
| 9,877,720 | B2 | 1/2018 | Worrell et al. |
| 9,877,782 | B2 | 1/2018 | Voegele et al. |
| 2005/0240219 | A1* | 10/2005 | Kahle ................. A61B 17/122 606/207 |

* cited by examiner

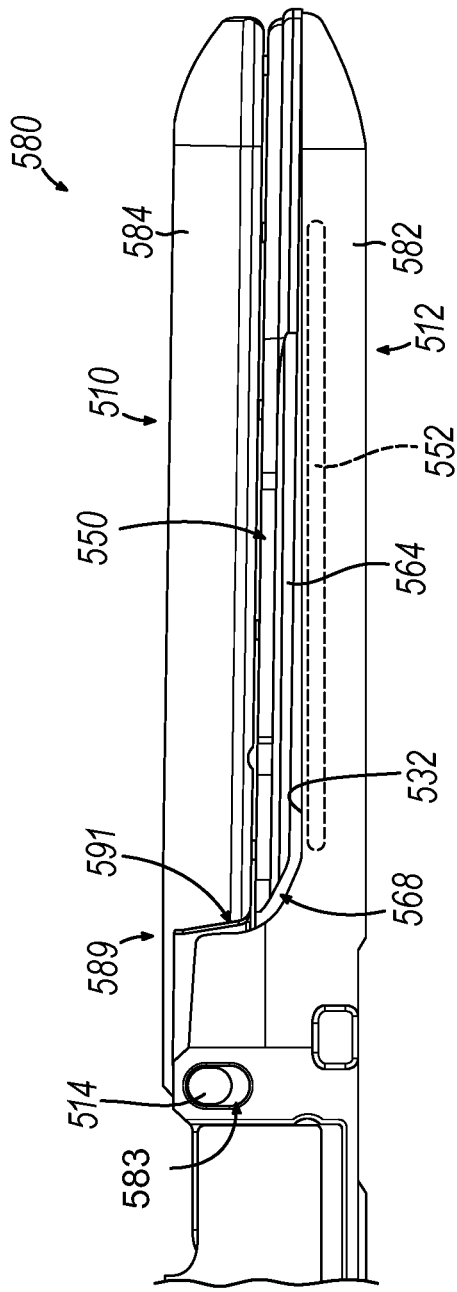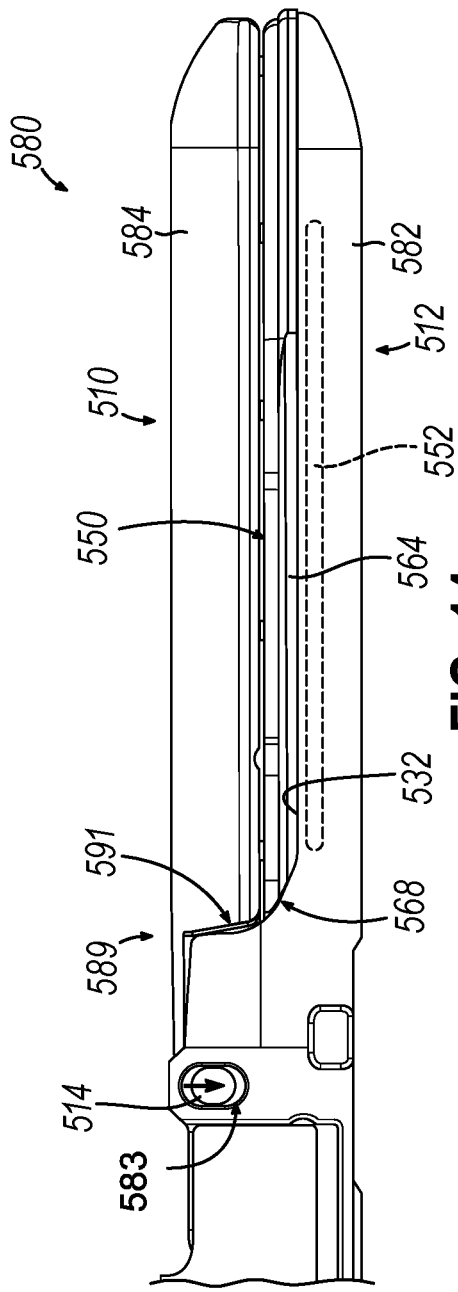

ELECTROSURGICAL INSTRUMENT WITH FLOATING JAW COMPONENT

PRIORITY

This application claims priority to U.S. Provisional Pat. App. No. 63/050,304, entitled "Jaw Gap Control," filed Jul. 10, 2020, the disclosure of which is incorporated by reference herein, in its entirety.

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein, in its entirety; U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein, in its entirety; U.S. Pat. No. 8,888,809, entitled "Surgical Instrument with Jaw Member," issued Nov. 18, 2014, the disclosure of which is incorporated by reference herein, in its entirety; U.S. Pat. No. 9,161,803, entitled "Motor Driven Electrosurgical Device with Mechanical and Electrical Feedback," issued Oct. 20, 2015, the disclosure of which is incorporated by reference herein, in its entirety; U.S. Pat. No. 9,877,720, entitled "Control Features for Articulating Surgical Device," issued Jan. 30, 2018, the disclosure of which is incorporated by reference herein, in its entirety; U.S. Pat. No. 9,545,253, entitled "Surgical Instrument with Contained Dual Helix Actuator Assembly," issued Jan. 17, 2017, the disclosure of which is incorporated by reference herein, in its entirety; and U.S. Pat. No. 9,526,565, entitled "Electrosurgical Devices," issued Dec. 27, 2016, the disclosure of which is incorporated by reference herein, in its entirety.

Some electrosurgical instruments include an end effector with at least one compliant feature. Examples of such instruments are described in U.S. Pat. No. 9,149,325, entitled "End Effector with Compliant Clamping Jaw," issued Oct. 6, 2015, the disclosure of which is incorporated by reference herein, in its entirety; and U.S. Pat. No. 9,877,782, entitled "Electrosurgical Instrument End Effector with Compliant Electrode," issued Jan. 30, 2018, the disclosure of which is incorporated by reference herein, in its entirety.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 13 depicts a side elevation view of another example of an end effector that may be incorporated into the electrosurgical instrument of FIG. 1, with the end effector in a closed configuration, and with a proximal region of an upper jaw in an upper position; and FIG. 14 depicts a side elevation view of the end effector of FIG. 13, with the end effector in a closed configuration, and with a proximal region of an upper jaw in a lower position.

Figure 1:
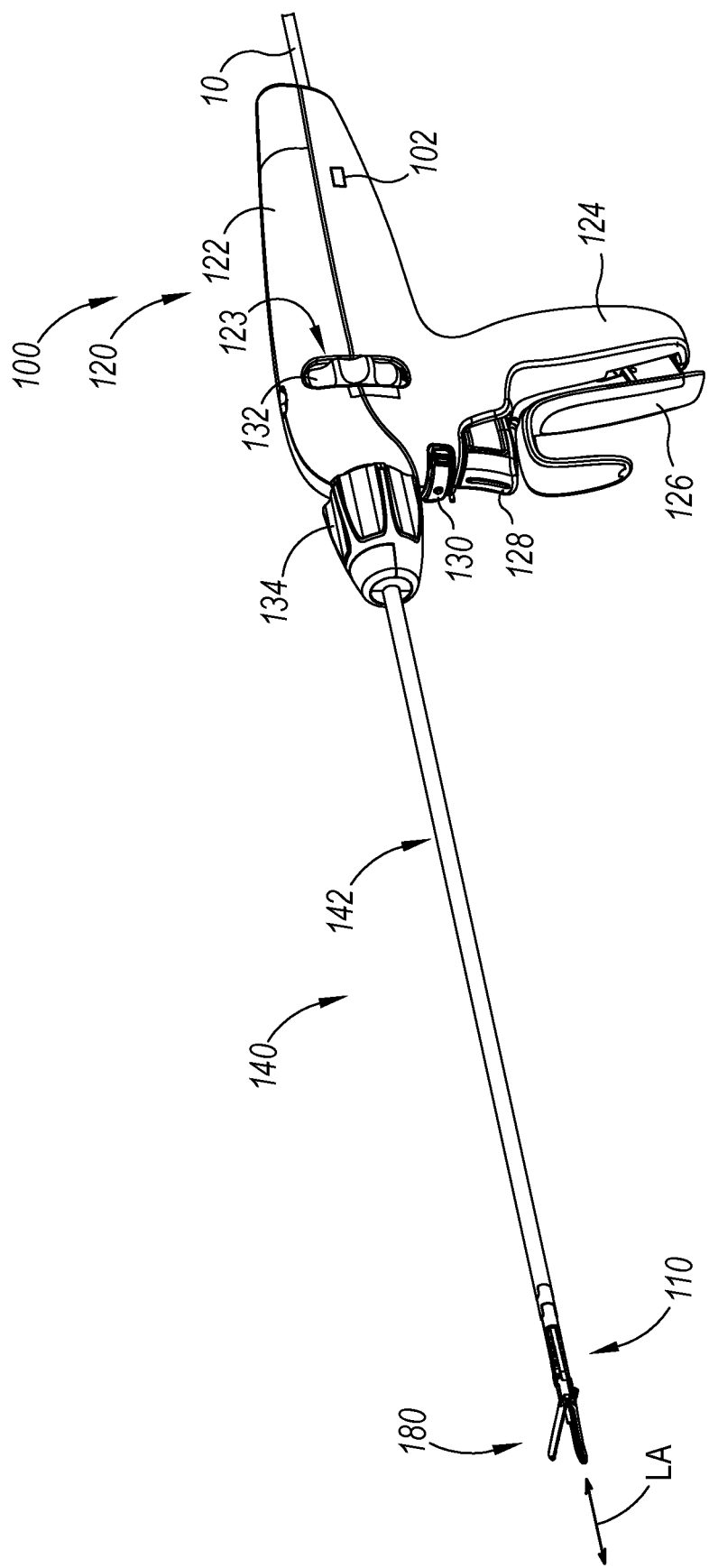
FIG. 1 depicts a perspective view of an exemplary electrosurgical instrument.

The drawings are not intended to be limiting in any way, and it is contemplated that various embodiments of the technology may be carried out in a variety of other ways, including those not necessarily depicted in the drawings.

The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Example of Electrosurgical Instrument

FIGS. 1-3C show an exemplary electrosurgical instrument (100). As best seen in FIG. 1, electrosurgical instrument (100) includes a handle assembly (120), a shaft assembly (140), an articulation assembly (110), and an end effector (180). As will be described in greater detail below, end effector (180) of electrosurgical instrument (100) is operable to grasp, cut, and seal or weld tissue (e.g., a blood vessel, etc.). In this example, end effector (180) is configured to seal or weld tissue by applying bipolar radio frequency (RF) energy to tissue. However, it should be understood electrosurgical instrument (100) may be configured to seal or weld tissue through any other suitable means that would be apparent to one skilled in the art in view of the teachings herein. For example, electrosurgical instrument (100) may be configured to seal or weld tissue via an ultrasonic blade, staples, etc. In the present example, electrosurgical instrument (100) is electrically coupled to a power source (not shown) via power cable (10).

The power source may be configured to provide all or some of the electrical power requirements for use of electrosurgical instrument (100). Any suitable power source may be used as would be apparent to one skilled in the art in view of the teachings herein. By way of example only, the power source may comprise a GEN04 or GEN11 sold by Ethicon Endo-Surgery, Inc. of Cincinnati, Ohio. In addition, or in the alternative, the power source may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein, in its entirety. While in the current example, electrosurgical instrument (100) is coupled to a power source via power cable (10), electrosurgical instrument (100) may contain an internal power source or plurality of power sources, such as a battery and/or supercapacitors, to electrically power electrosurgical instrument (100). Of course, any suitable combination of power sources may be utilized to power electrosurgical instrument (100) as would be apparent to one skilled in the art in view of the teaching herein.

Handle assembly (120) is configured to be grasped by an operator with one hand, such that an operator may control and manipulate electrosurgical instrument (100) with a single hand. Shaft assembly (140) extends distally from handle assembly (120) and connects to articulation assembly (110). Articulation assembly (110) is also connected to a proximal end of end effector (180). As will be described in greater detail below, components of handle assembly (120) are configured to control end effector (180) such that an operator may grasp, cut, and seal or weld tissue. Articulation assembly (110) is configured to deflect end effector (180) from the longitudinal axis (LA) defined by shaft assembly (140).

Handle assembly (120) includes a control unit (102) housed within a body (122), a pistol grip (124), a jaw closure trigger (126), a knife trigger (128), an activation button (130), an articulation control (132), and a knob (134). As will be described in greater detail below, jaw closure trigger (126) may be pivoted toward and away from pistol grip (124) and/or body (122) to open and close jaws (182, 184) of end effector (180) to grasp tissue. Additionally, knife trigger (128) may be pivoted toward and away from pistol grip (124) and/or body (122) to actuate a knife member (176) within the confines of jaws (182, 184) to cut tissue captured between jaws (182, 184). Further, activation button (130) may be pressed to apply radio frequency (RF) energy to tissue via electrode surfaces (194, 196) of jaws (182, 184), respectively.

Body (122) of handle assembly (120) defines an opening (123) in which a portion of articulation control (132) protrudes from. Articulation control (132) is rotatably disposed within body (122) such that an operator may rotate the portion of articulation control (132) protruding from opening (123) to rotate the portion of articulation control (132) located within body (122). Rotation of articulation control (132) relative to body (122) is configured to bend articulation section (110) in order to drive deflection of end effector (180) from the longitudinal axis (LA) defined by shaft assembly (140). Articulation control (132) and articulation section (110) may include any suitable features to drive deflection of end effector (180) from the longitudinal axis (LA) defined by shaft assembly (140) as would be apparent to one skilled in the art in view of the teachings herein.

Knob (134) is rotatably disposed on the distal end of body (122) and configured to rotate end effector (180), articulation assembly (110), and shaft assembly (140) about the longitudinal axis (LA) of shaft assembly (140) relative to handle assembly (120). While in the current example, end effector (180), articulation assembly (110), and shaft assembly (140) are rotated by knob (134), knob (134) may be configured to rotate end effector (180) and articulation assembly (110) relative to selected portions of shaft assembly (140). Knob (134) may include any suitable features to rotate end effector (180), articulation assembly (110), and shaft assembly (140) as would be apparent to one skilled in the art in view of the teachings herein.

Figure 3:
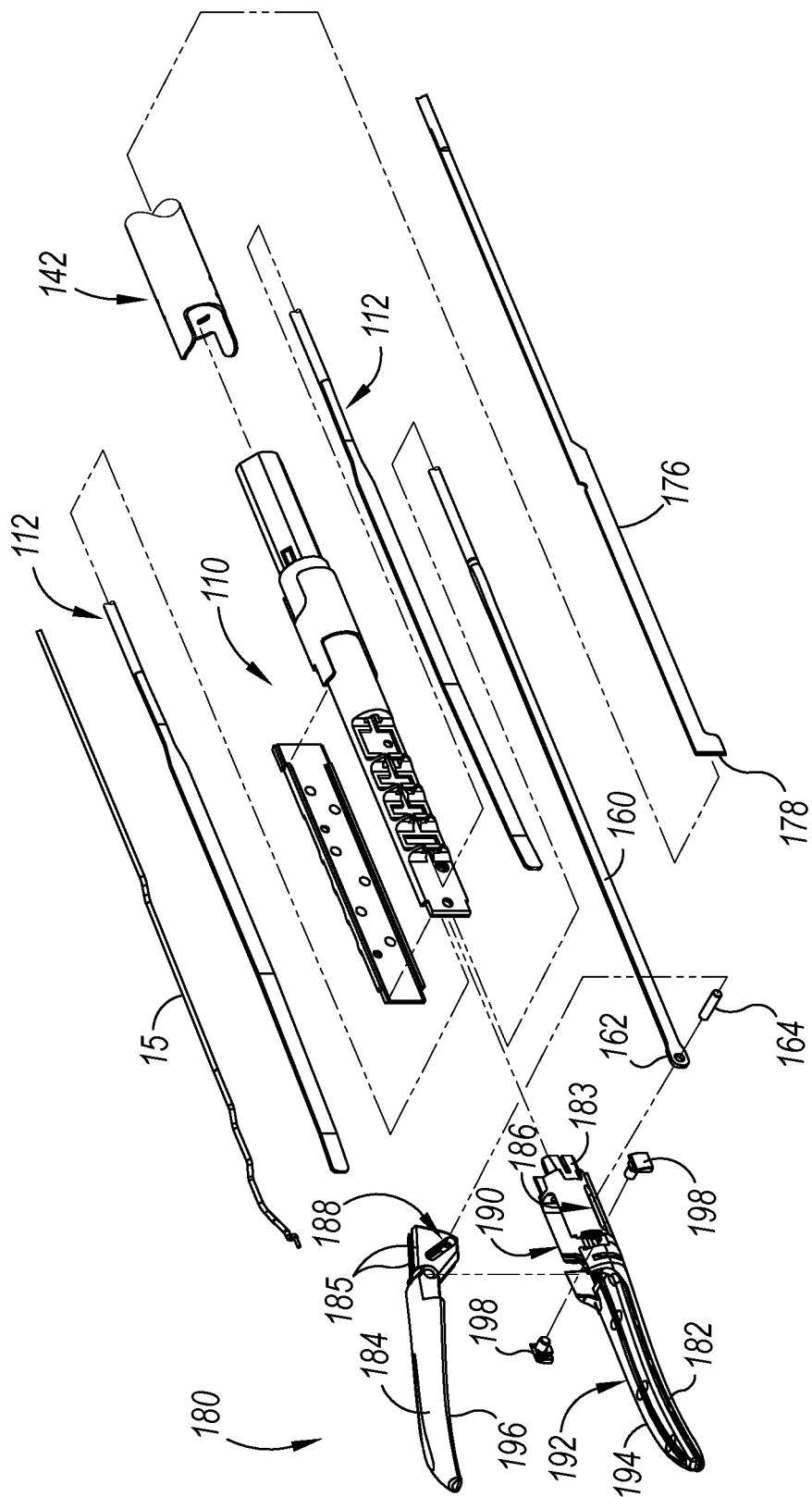
FIG. 3 depicts an exploded view of the articulation assembly and end effector of FIG. 2.

Shaft assembly (140) includes distal portion (142) extending distally from handle assembly (120), and a proximal portion (144) (see FIGS. 4A-4B) housed within the confines of body (122) of handle assembly (120). As best shown in FIG. 3, shaft assembly (140) houses a jaw closure connector (160) that couples jaw closure trigger (126) with end effector (180). Additionally, shaft assembly (140) houses a portion of knife member extending between distal cutting edge (178) and knife trigger (128). Shaft assembly (140) also houses actuating members (112) that couple articulation assembly (110) with articulation control (132); as well as an electrical connecter (15) that operatively couples electrode surfaces (194, 196) with activation button (130). As will be described in greater detail below, jaw closure connector (160) is configured to translate relative to shaft assembly (140) to open and close jaws (182, 184) of end effector (180); while knife member (176) is coupled to knife trigger (128) of handle assembly (120) to translate distal cutting edge (178) within the confines of end effector (180); and activation button (130) is configured to activate electrode surface (194, 196).

Figure 2:
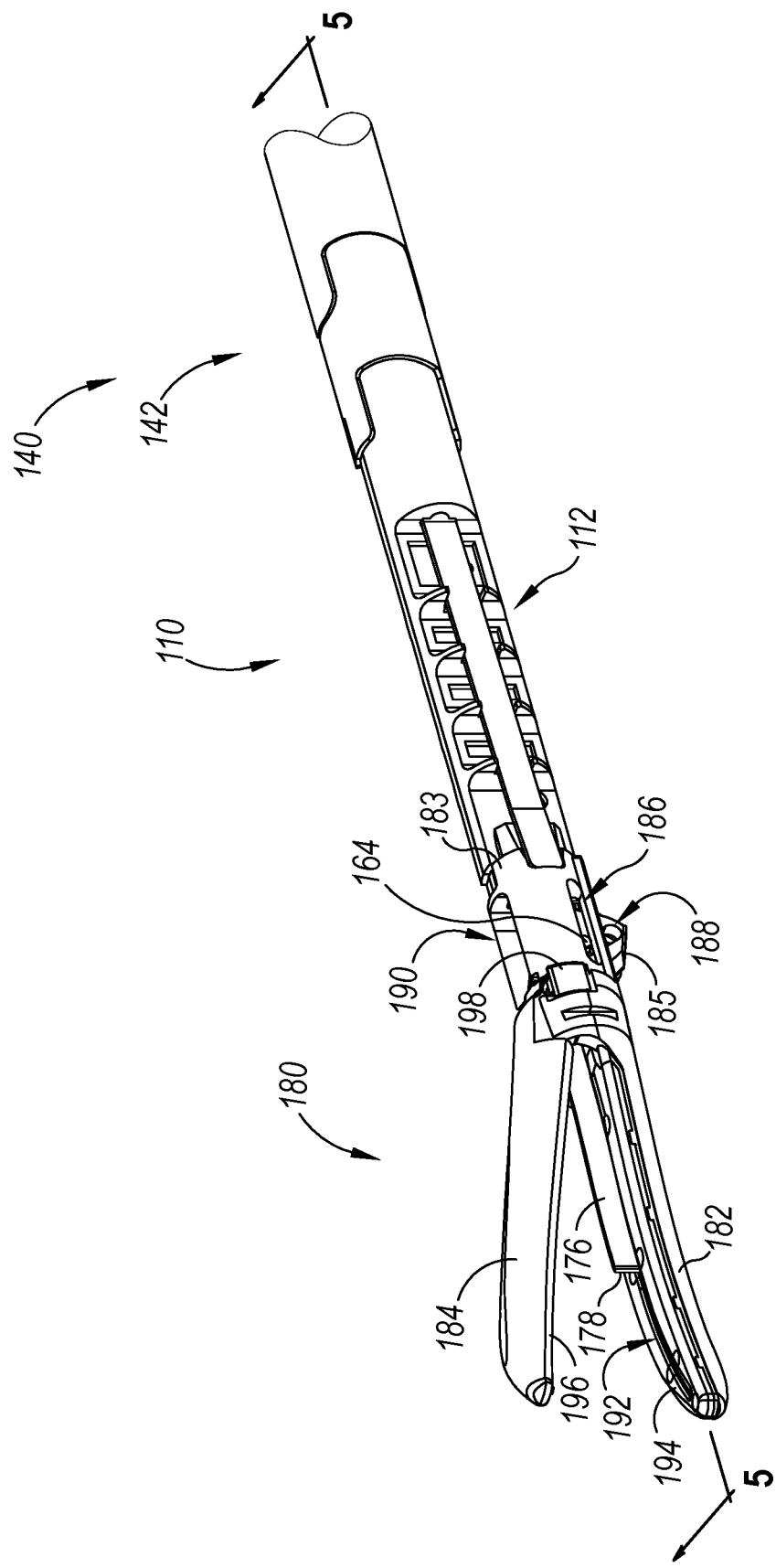
FIG. 2 depicts a perspective view of an exemplary articulation assembly and end effector of the electrosurgical instrument of FIG. 1.
Figure 5A:
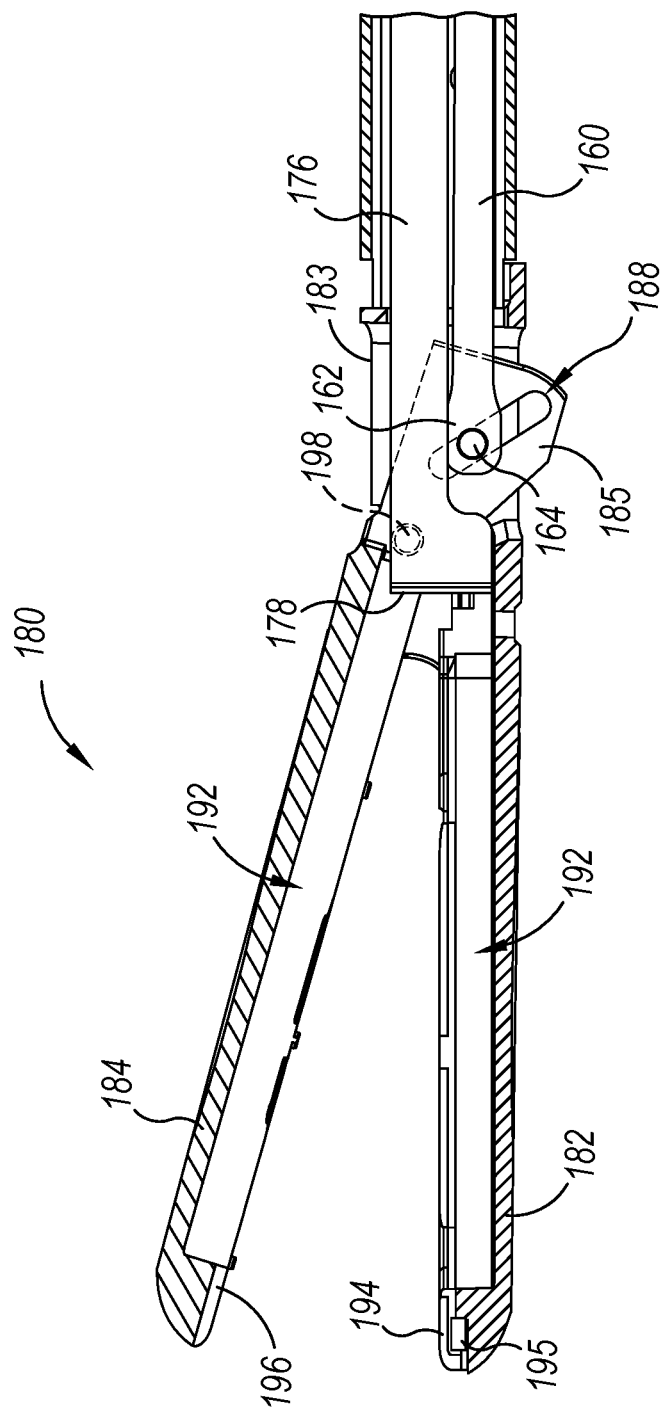
FIG. 5A depicts a cross-sectional side view of the end effector of FIG. 2, where the end effector is in the open and unfired state, taken along line 5-5 of FIG. 2.
Figure 5B:
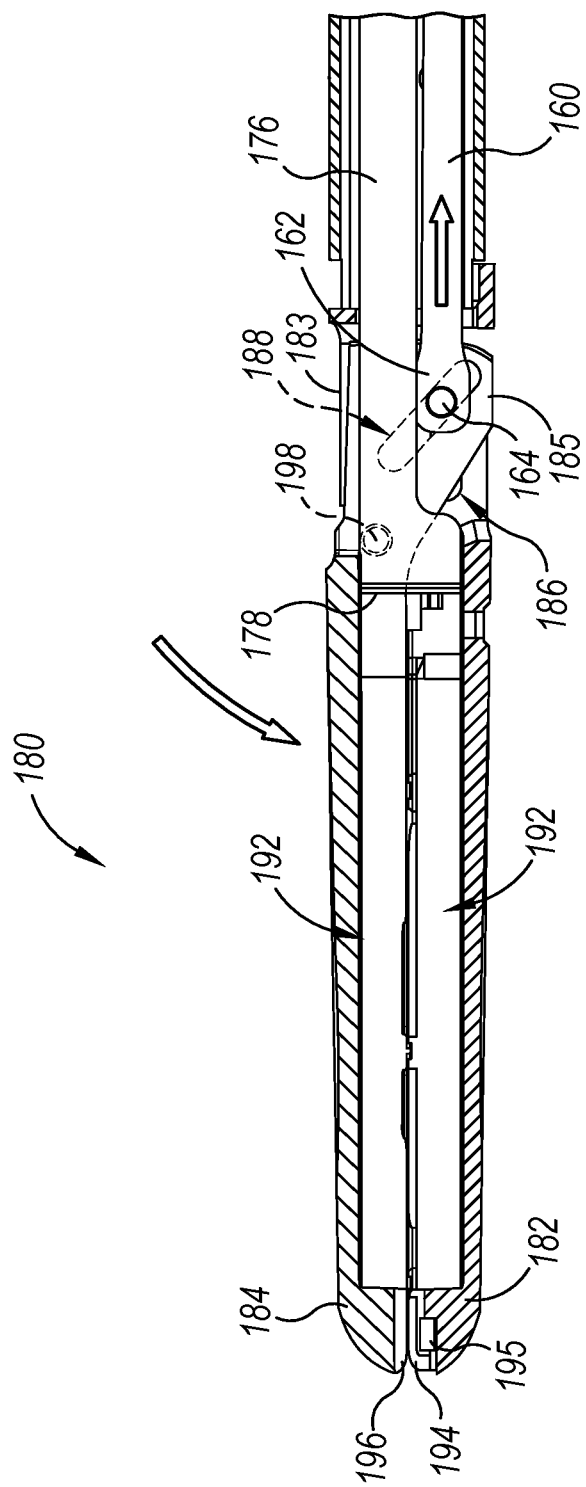
FIG. 5B depicts a cross-sectional side view of the end effector of FIG. 2, where the end effector is in the closed and unfired state, taken along line 5-5 of FIG. 2.
Figure 5C:
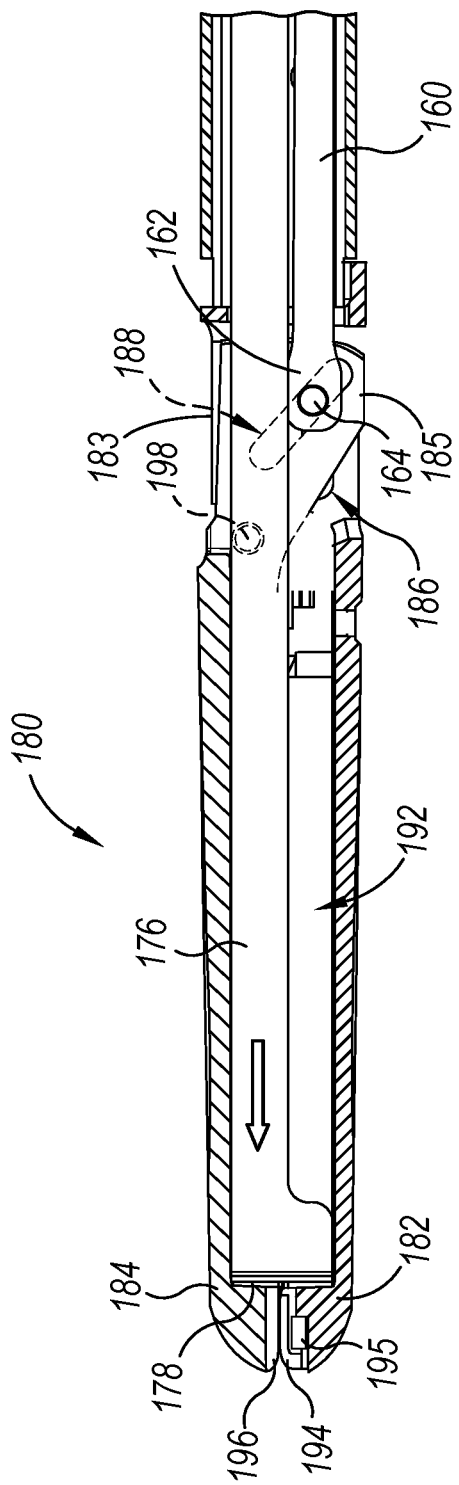
FIG. 5C depicts a cross-sectional side view of the end effector of FIG. 2, where the end effector is in the closed and fired state, taken along line 5-5 of FIG. 2.

As best seen in FIGS. 2-3, end effector (180) includes lower jaw (182) pivotally coupled with upper jaw (184) via pivot couplings (198). Lower jaw (182) includes a proximal body (183) defining a slot (186), while upper jaw (184) includes proximal arms (185) defining a slot (188). Lower jaw (182) also defines a central channel (190) that is configured to receive proximal arms (185) of upper jaw (184), portions of knife member (176), jaw closure connecter (160), and pin (164). Slots (186, 188) each slidably receive pin (164), which is attached to a distal coupling portion (162) of jaw closure connector (160). Additionally, as best seen in FIGS. 5A-5C, lower jaw (182) includes a force sensor (195) located at a distal tip of lower jaw (182). Force sensor (195) may be in communication with control unit (102). Force sensor (195) may be configured to measure the closure force generated by pivoting jaws (182, 184) into a closed configuration in accordance with the description herein. Additionally, force sensor (195) may communicate this data to control unit (102). Any suitable components may be used for force sensor (195) as would be apparent to one skilled in art in view of the teachings herein. For example, force sensor (195) may take the form of a strain gauge.

While in the current example, a force sensor (195) is incorporated into instrument (100) and is in communication with control unit (102), any other suitable sensors or feedback mechanisms may be additionally or alternatively incorporated into instrument (100) while in communication with control unit (102) as would be apparent to one skilled in the art in view of the teachings herein. For instance, an articulation sensor or feedback mechanism may be incorporated into instrument (100), where the articulation sensor communicates signals to control unit (102) indicative of the degree end effector (180) is deflected from the longitudinal axis (LA) by articulation control (132) and articulation section (110).

As will be described in greater detail below, jaw closure connector (160) is operable to translate within central channel (190) of lower jaw (182). Translation of jaw closure connector (160) drives pin (164). As will also be described in greater detail below, with pin (164) being located within both slots (186, 188), and with slots (186, 188) being angled relative to each other, pin (164) cams against proximal arms (185) to pivot upper jaw (184) toward and away from lower jaw (182) about pivot couplings (198). Therefore, upper jaw (184) is configured to pivot toward and away from lower jaw (182) about pivot couplings (198) to grasp tissue.

The term "pivot" does not necessarily require rotation about a fixed axis and may include rotation about an axis that moves relative to end effector (180). Therefore, the axis at which upper jaw (184) pivots about lower jaw (182) may translate relative to both upper jaw (184) and lower jaw (182). Any suitable translation of the pivot axis may be used as would be apparent to one skilled in the art in view of the teachings herein.

Lower jaw (182) and upper jaw (184) also define a knife pathway (192). Knife pathway (192) is configured to slidably receive knife member (176), such that knife member (176) may be retracted (as shown in FIGS. 5A-5B), and advanced (as shown in FIG. 5C), to cut tissue captured between jaws (182, 184). Lower jaw (182) and upper jaw (184) each comprise a respective electrode surface (194, 196). The power source may provide RF energy to electrode surfaces (194, 196) via electrical coupling (15) that extends through handle assembly (120), shaft assembly (140), articulation assembly (110), and electrically couples with one or both of electrode surfaces (194, 196). Electrical coupling (15) may selectively activate electrode surfaces (194, 196) in response to an operator pressing activation button (130). In some instances, control unit (102) may couple electrical coupling (15) with activation button (130), such that control unit (102) activates electrode surfaces (194, 196) in response to operator pressing activation button (130). Control unit (102) may have any suitable components in order to perform suitable functions as would be apparent to one skilled in the art in view of the teachings herein. For instance, control unit (102) may have a processor, memory unit, suitable circuitry, etc.

FIGS. 4A-5C show an exemplary use of instrument (100) for end effector (180) to grasp, cut, and seal/weld tissue. As described above, and as shown between FIGS. 4A-4B and 5A-5B, jaw closure trigger (126) may be pivoted toward and away from pistol grip (124) and/or body (122) to open and close jaws (182, 184) of end effector (180) to grasp tissue. In particular, as will be described in greater detail below, pivoting jaw closure trigger (126) toward pistol grip (124) may proximally actuate jaw closure connector (160) and pin (164), which in turn cams against slots (188) of proximal arms (185) of upper jaw (184), thereby rotating upper jaw (184) about pivot couplings (198) toward lower jaw (182) such that jaws (182, 184) achieve a closed configuration.

Handle assembly (120) further includes a yoke assembly (200) that is slidably coupled along proximal portion (144) of shaft assembly (140). Yoke assembly (200) is operatively coupled with jaw closure connector (160) such that translation of yoke assembly (200) relative to proximal portion (144) of shaft assembly (140) translates jaw closure connector (160) relative to shaft assembly (140).

Figure 4A:
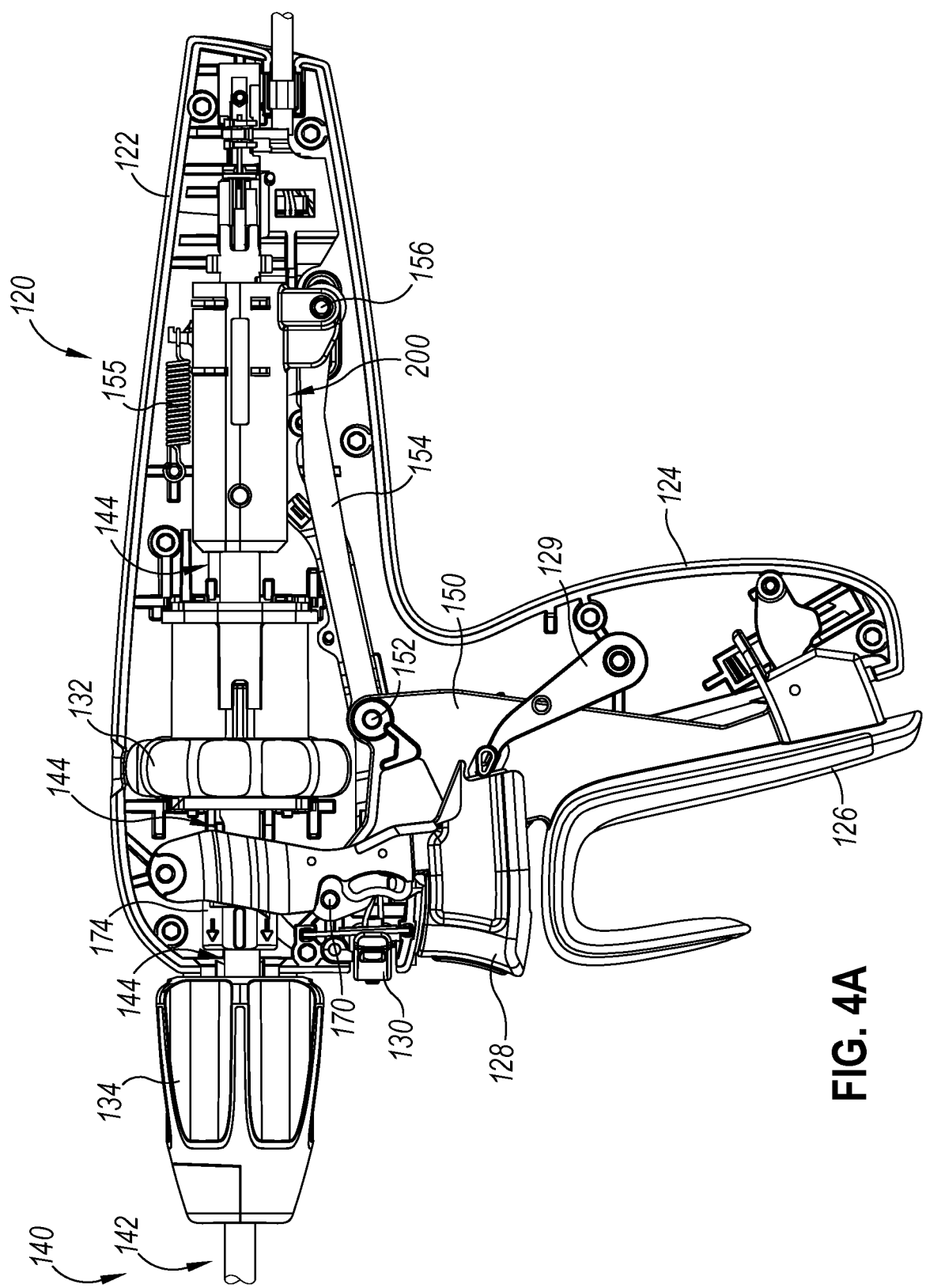
FIG. 4A depicts a side elevational view of a handle assembly of the electrosurgical instrument of FIG. 1, where the end effector is in an open and unfired state, where a portion of the handle assembly is omitted for purposes of clarity.
Figure 4B:
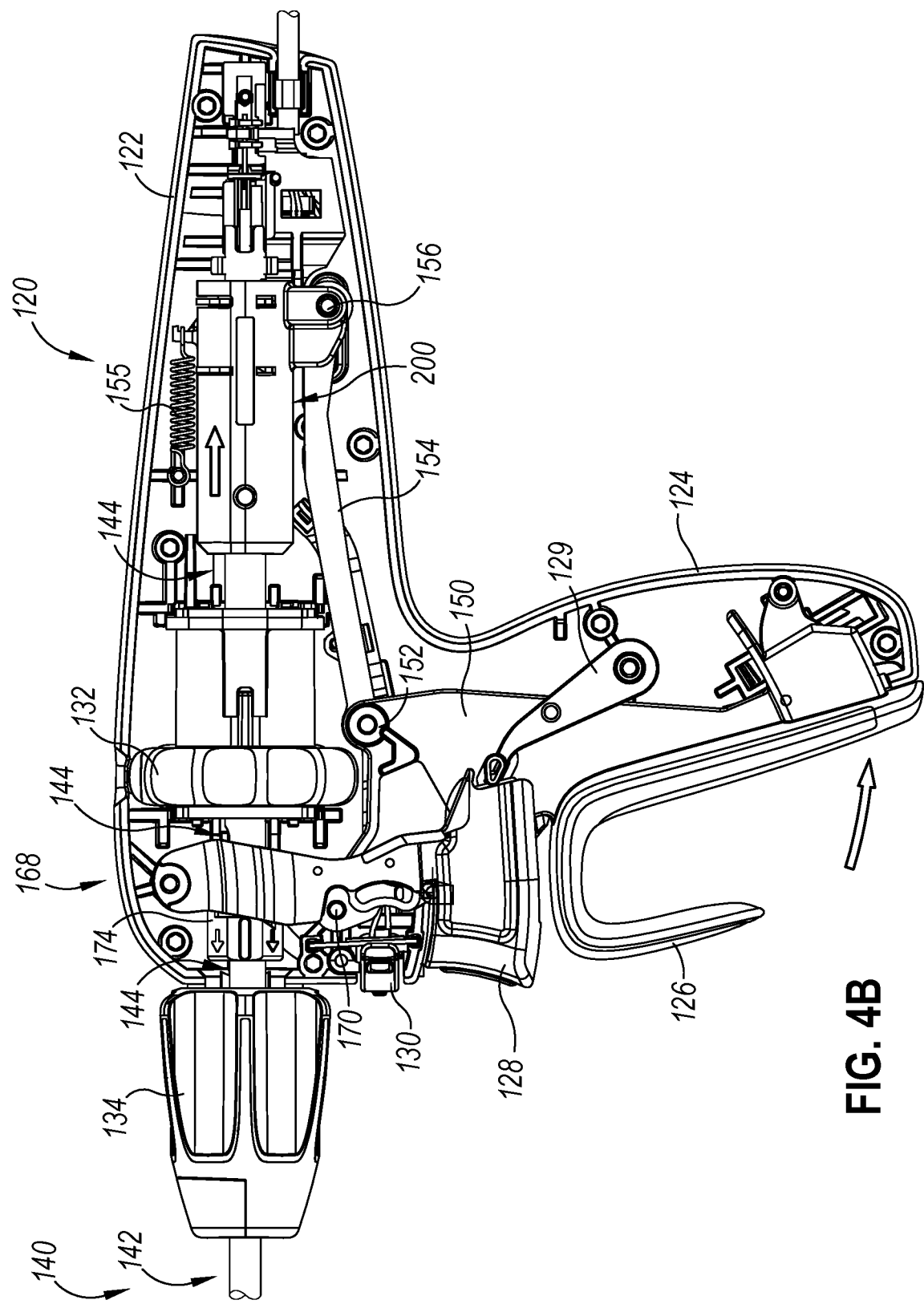
FIG. 4B depicts a side elevational view of the handle assembly of FIG. 4A, where the end effector is in a closed and unfired state, where a portion of the handle assembly is omitted for purposes of clarity.
Figure 4C:
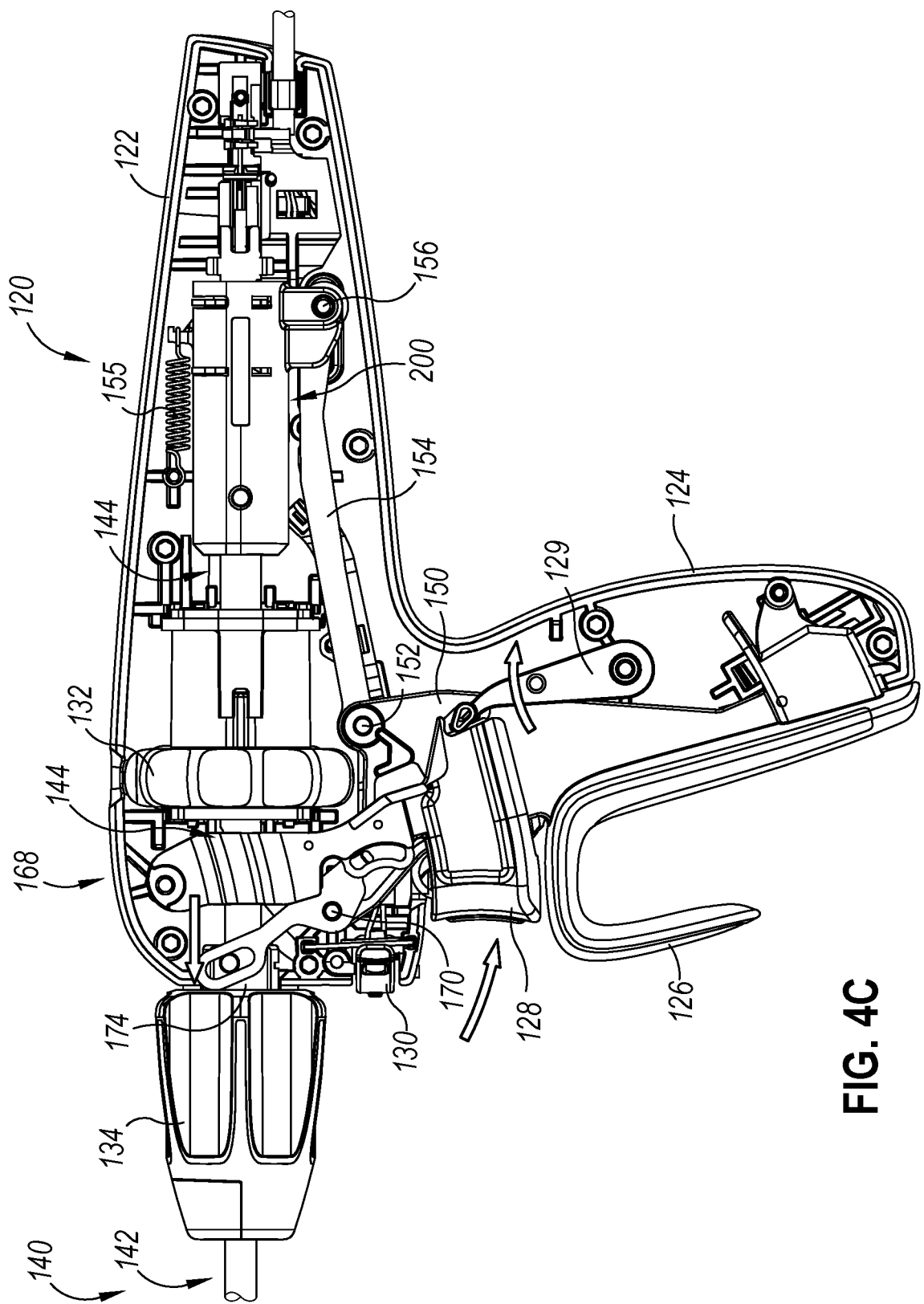
FIG. 4C depicts a side elevational view of the handle assembly of FIG. 4A, where the end effector is in a closed and fired state, where a portion of the handle assembly is omitted for purposes of clarity.

As best seen in FIGS. 4A-4C, yoke assembly (200) is coupled to a body (150) of jaw closure trigger (126) via a link (154). Link (154) is pivotally coupled with yoke assembly (200) via pin (156); while link (154) is also pivotally coupled with body (150) of jaw closure trigger (126) via pin (152). Additionally, jaw closure trigger (126) is pivotally coupled with body (122) of handle assembly (120) via pin (170). Therefore, as shown between FIGS. 4A-4B, an operator may pull jaw closure trigger (126) toward pistol grip (124), thereby rotating jaw closure trigger (126) about pin (170). Rotation of jaw closure trigger (126) leads to rotation of link (154) about both pins (152, 156), which in turn drives yoke assembly (200) in the proximal direction along proximal portion (144) of shaft assembly (140).

As described above, jaw closure connector (160) extends within shaft assembly (140), articulation section (110), and central channel (190) of lower jaw (182). As also mentioned above, jaw closure connector (160) is attached to pin (164). Therefore, as seen between FIGS. 5A-5B, proximal translation of yoke assembly (200) leads to proximal translation of pin (164), which in turn cams against slots (188) of proximal arms (185) of upper jaw (184), thereby rotating upper jaw (184) about pivot couplings (198) toward lower jaw (182) such that jaws (182, 184) achieve a closed configuration.

As best seen in FIGS. 4A-4C, yoke assembly (200) is also coupled with a bias spring (155). Bias spring (155) is also coupled to a portion of body (122), such that bias spring (155) biases yoke assembly (200) to the position shown in FIG. 4A (associated with the open configuration of end effector (180) as shown in FIG. 5A). Therefore, if an operator releases jaw closure trigger (126), bias spring (155) will translate yoke assembly (200) to the position shown in FIG. 4A, thereby opening jaws (182, 184) of end effector (180).

As described above, and as shown between FIGS. 4B-4C and 5B-5C, knife trigger (128) may be pivoted toward and away from body (122) and/or pistol grip (124) to actuate knife member (176) within knife pathway (192) of jaws (182, 184) to cut tissue captured between jaws (182, 184). In particular, handle assembly (120) further includes a knife coupling body (174) that is slidably coupled along proximal portion (144) of shaft assembly (140). Knife coupling body (174) is coupled with knife member (176) such that translation of knife coupling body (174) relative to proximal portion (144) of shaft assembly (140) translates knife member (176) relative to shaft assembly (140).

As best seen in FIGS. 4B-4C and 5B-5C, knife coupling body (174) is coupled a knife actuation assembly (168) such that as knife trigger (128) pivots toward body (122) and/or pistol grip (124), knife actuation assembly (168) drives knife coupling body (174) distally, thereby driving knife member (176) distally within knife pathway (192). Because knife coupling body (174) is coupled to knife member (176), knife member (176) translates distally within shaft assembly (140), articulation section (110), and within knife pathway (192) of end effector (180), as best shown between FIGS. 5B-5C. Knife member (176) includes distal cutting edge (178) that is configured to sever tissue captured between jaws (182, 184). Therefore, pivoting knife trigger (128) causes knife member (176) to actuate within knife pathway (192) of end effector (180) to sever tissue captured between jaws (182, 184).

Knife trigger (128) is biased to the positions seen in FIGS. 4A-4B (associated with the knife member (176) in the retracted position) by a bias arm (129). Bias arm (129) may include any suitable biasing mechanism as would be apparent to one having ordinary skill in the art in view of the teachings herein. For instance, bias arm (129) may include a torsion spring. Therefore, if an operator releases knife trigger (128), bias arm (129) returns knife trigger (128) to the position shown in FIGS. 4A-4B, thereby translating knife member (176) toward the retracted position.

With distal cutting edge (178) of knife member (176) actuated to the advance position (position shown in FIG. 5C), an operator may press activation button (130) to selectively activate electrode surfaces (194, 196) of jaws (182, 184) to weld/seal severed tissue that is captured between jaws (182, 184). It should be understood that the operator may also press activation button (130) to selectively activate electrode surfaces (194, 196) of jaws (182, 184) at any suitable time during exemplary use. Therefore, the operator may also press activation button (130) while knife member (176) is retracted as shown in FIGS. 3A-3B. Next, the operator may release jaw closure trigger (128) such that jaws (182, 184) pivot into the opened configuration, releasing tissue.

II. Example of End Effector with Floating Jaw Component

As mentioned above, end effector (180) is configured to grasp, sever, and weld/seal tissue. In particular, jaw (184) may pivot relative to jaw (182) in order to grasp tissue, while knife member (176) is configured to actuate within jaws (182, 184) in order to sever tissue that is grasped between jaws (182, 184). Electrode surfaces (194, 196) may be activated while jaws (182, 184) grasp tissue in order to weld/seal tissue captured between jaws (182, 184). While welding/sealing tissue captured between jaws (182, 184), an appropriate gap distance between electrode surfaces (194, 196) may be desirable along the entire length of electrode surfaces (194, 196). By way of example only, it may be desirable to provide a gap distance between electrode surfaces (194, 196) that ranges from approximately 0.002 inches to approximately 0.006 inches. If adjacent portions of electrode surfaces (194, 196) that cooperatively grasp tissue form a gap distance that is too small, tissue grasped between electrode surfaces (194, 196) may become crushed, damaged, etc. Additionally, if the gap distance is too small, electrode surfaces (194, 196) may come into incidental contact with each other to cause an undesirable short circuit. Conversely, if adjacent portions of electrode surfaces (194, 196) that cooperatively grasp tissue form a gap distance that is too large, electrode surfaces (194, 196) may not properly weld/seal tissue that is grasped between electrode surfaces (194, 196).

In some instances, the gap distance between electrode surfaces (194, 196) may deviate along the length of electrode surfaces (194, 196) such that a proximal portion of electrode surfaces (194, 196) form a gap distance of a first magnitude; and a distal portion of electrode surfaces (194, 196) form a gap distance of a second magnitude. In some such instances, the non-uniform gap distance along the length of electrode surfaces (194, 196) may be caused by deviations within manufacturing tolerances, such that different end effectors (180) provide different deviations in gap distances along the length of such end effectors (180) as a natural result of manufacturing processes. For instance, tolerances in the manufacture of jaws (182, 184), electrode surfaces (194, 196), slots (186, 188), pin (164), and/or other components may contribute to tolerance-related deviations from the desired gap distance between electrode surfaces (194, 196) and gap distance consistency along the length of electrode surfaces (194, 196).

Regardless of the cause, when the gap distance deviates along the length of an end effector (180), a first longitudinal region of electrode surfaces (194, 196) may create an acceptable tissue seal/weld, while a second longitudinal region of electrode surfaces (194, 196) may have too large or too small a gap distance that may cause undesirable effects as mentioned above. It may therefore be desirable to provide a form of end effector (180) that accommodates manufacturing tolerances and reliably provides a gap distance that achieves the desired effects along the entire length of electrode surfaces (194, 196). In other words, it may be desirable to provide a modified form of end effector (180) that includes one or more features to neutralize or absorb tolerances from the manufacturing process. An example of such an alternative form of end effector (180) is described in greater detail below.

Figure 6:
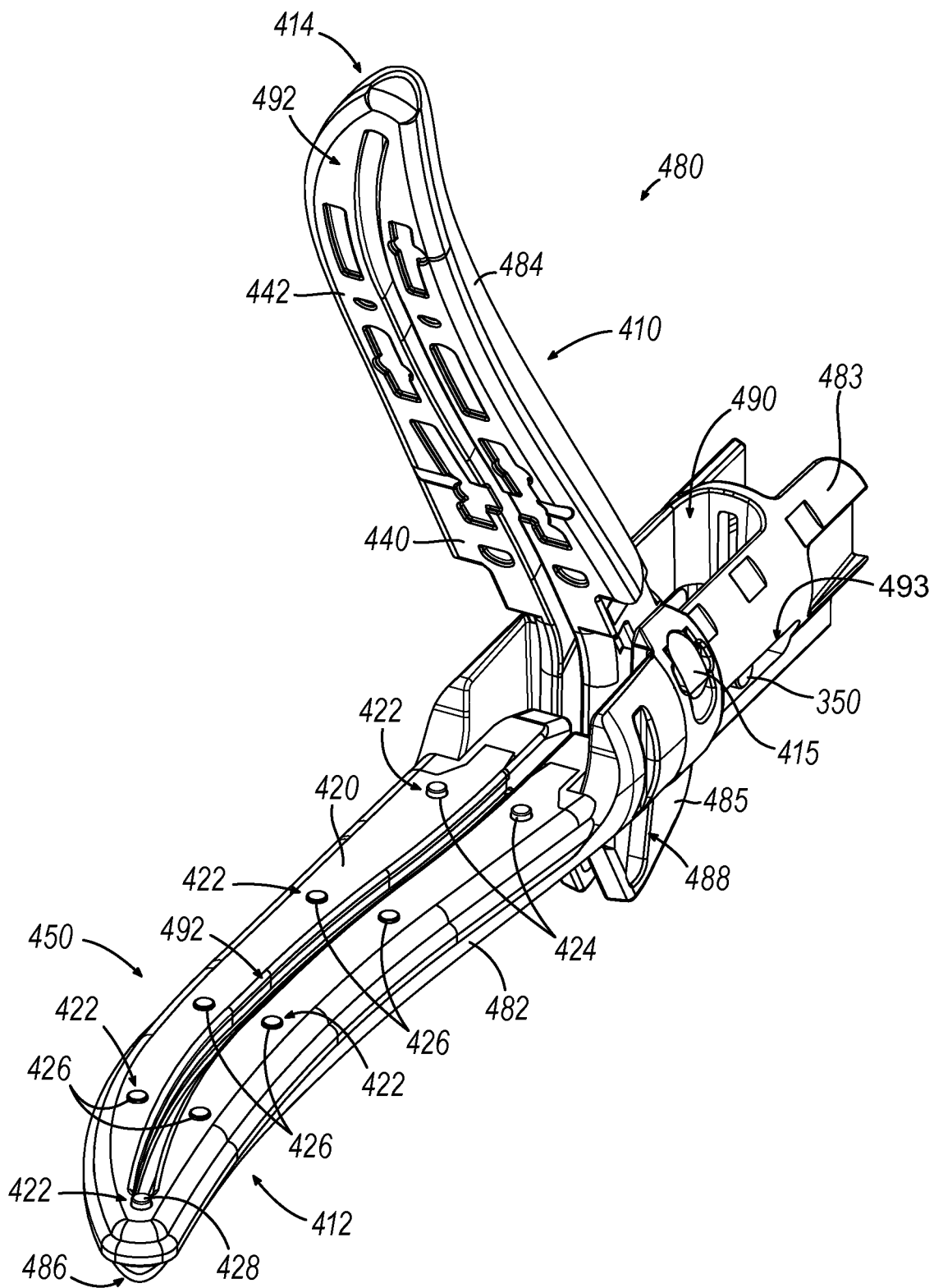
FIG. 6 depicts a perspective view of another example of an end effector that may be incorporated into the electrosurgical instrument of FIG. 1.

FIG. 6 shows an example of another end effector (480) that may be readily incorporated into electrosurgical instrument (100) in replacement of end effector (180) described above. End effector (480) is substantially similar to end effector (180) described above, with differences elaborated below. As will be described in greater detail below, end effector (480) includes a lower electrode assembly (450) that is configured to absorb (or otherwise account for) tolerance stacking and thereby promote an acceptable weld/seal of tissue grasped by end effector (480) in accordance with the description herein.

End effector (480) of the present example includes an upper jaw (410) and a lower jaw (412). Except for the differences described in greater detail below, upper jaw (410) and lower jaw (412) may be configured and operable like upper jaw (184) and lower jaw (182), respectively, described above. Upper jaw (410) is configured to pivot relative to lower jaw (412) in order to grasp tissue between jaws (410, 412).

Figure 7:
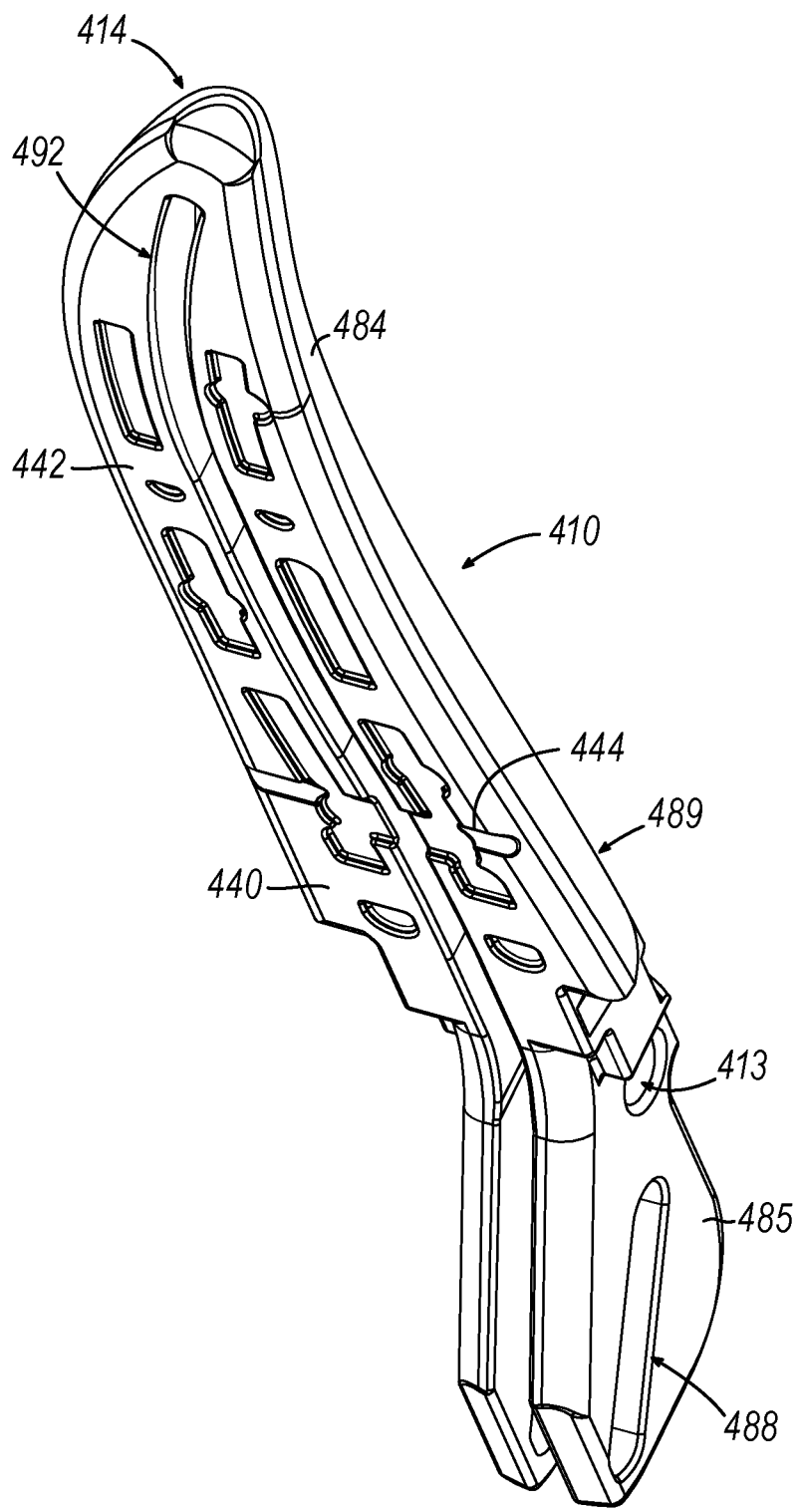
FIG. 7 depicts a perspective view of an upper jaw of the end effector of FIG. 6.

As best shown in FIG. 7, upper jaw (410) includes an upper jaw body (484) and a pair of proximal arms (485) that extend proximally from upper jaw body (484). Proximal arms (485) may be configured and operable like proximal arms (185) described above. proximal arms (485) define a slot (488), which is configured and operable like slot (188) described above. Slot (488) is configured to receive a pin (350), which is operable to drive pivotal movement of upper jaw (410) relative to lower jaw (412) as will be described in greater detail below. An aperture (413) in upper jaw (410) is configured to receive another pin (415), which is configured to provide a pivot axis as will be described in greater detail below.

Upper jaw (410) further includes a proximal electrode surface (440) and a distal electrode surface (442). Electrode surfaces (440, 442) are separated by a transverse gap (444). In some variations, gap (444) is omitted, such that upper jaw (410) includes only one electrode surface (440, 442). Electrode surfaces (440, 442) may be configured and operable like electrode surface (196) described above. Electrode surfaces (440, 442) may thus be coupled with a power source such that the power source may provide RF energy to electrode surfaces (440, 442). An operator may thus selectively activate electrode surfaces (440, 442) by pressing activation button (130) in accordance with the description above.

Figure 8:
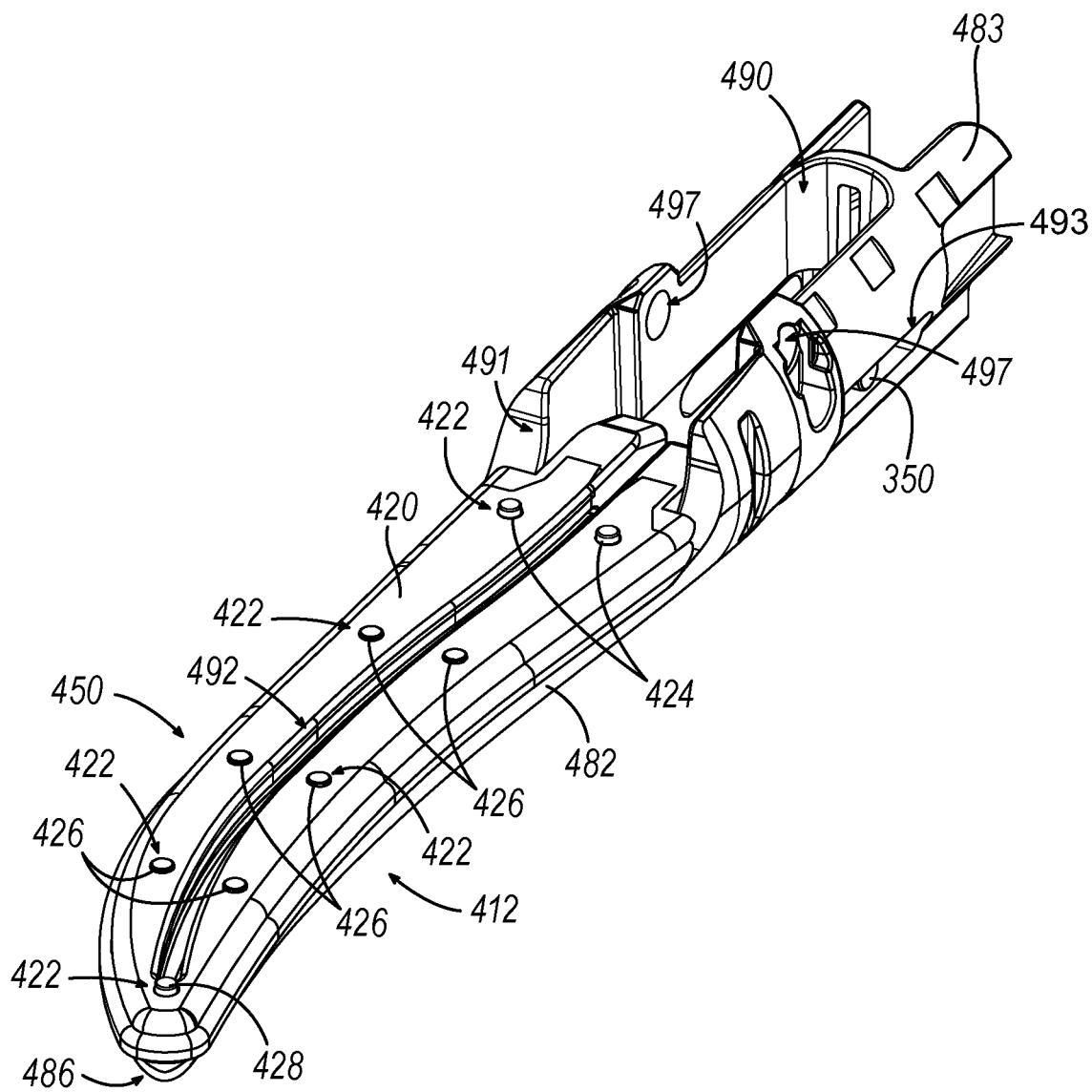
FIG. 8 depicts a perspective view of a lower jaw of the end effector of FIG. 6.
Figure 9:
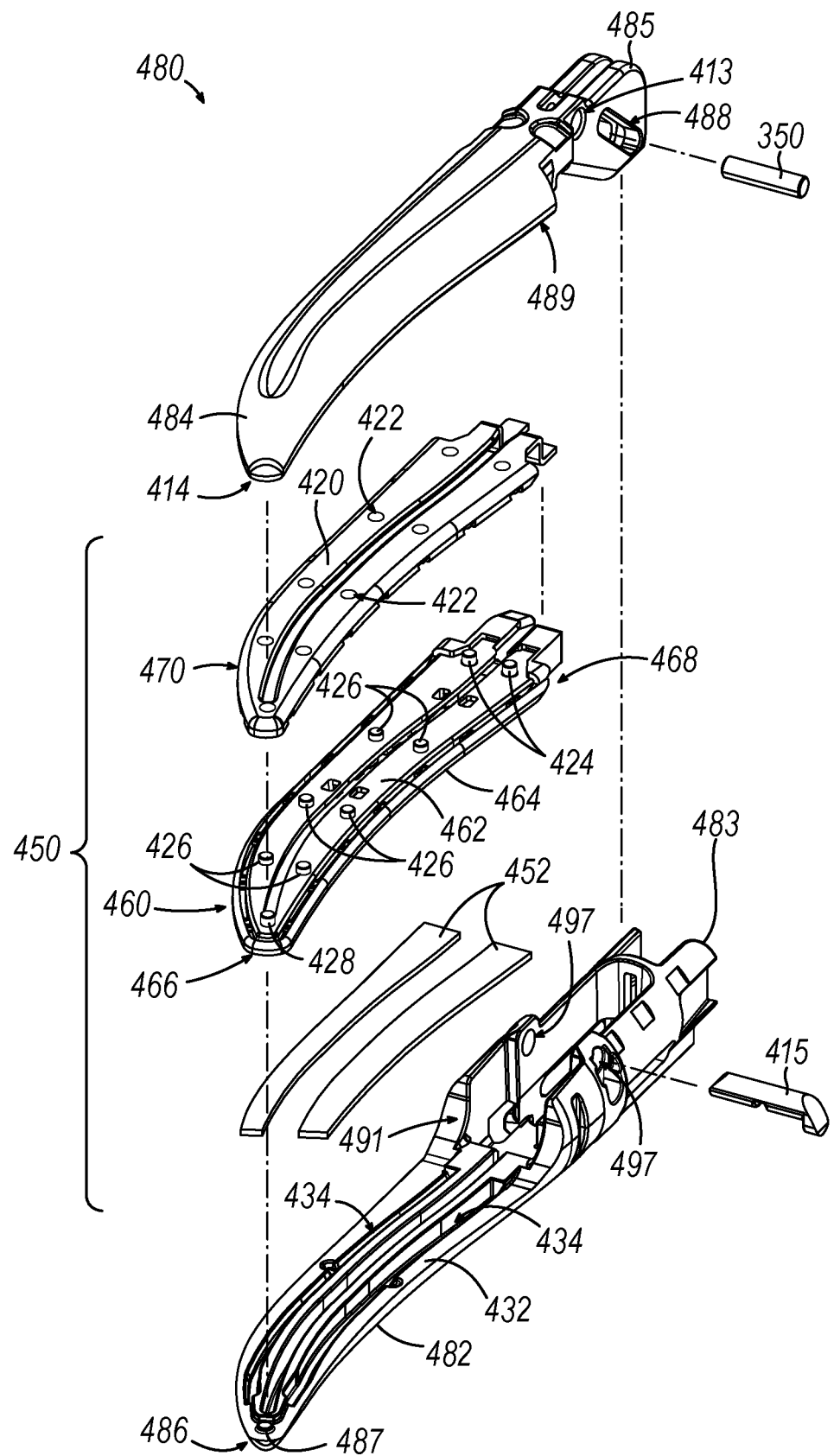
FIG. 9 depicts an exploded perspective view of the end effector of FIG. 6.

As best shown FIGS. 8-9, lower jaw (412) includes a lower jaw body (482) and a proximal body (483) that extends proximally from lower jaw body (482). Proximal body (483) may be configured and operable like proximal body (183) described above. Proximal body (483) defines a central channel (490) and a slot 493, which are respectively configured and operable like central channel (190) and slot (186) described above. Slot (493) of lower jaw (412) is configured to receive the same pin (350) as slot (488) of upper jaw (410). As noted above, this pin (350) is operable to drive pivotal movement of upper jaw (410) relative to lower jaw (412) as described above in the context of FIGS. 5A-5B. Pivotal movement of upper jaw (410) toward and away from lower jaw (412) is driven via translation of pin (350) within slots (493, 488). Pin (350) of this example is thus configured and operable like pin (164) described above. Proximal body (483) further defines an aperture (197) that is configured to receive the same pin (415) as aperture (413) of upper jaw (410). Pin (415) is configured to provide a pivot axis for the pivotal movement of upper jaw (410) relative to lower jaw (412). As noted above, upper jaw (410) is configured to pivot relative to lower jaw (412) in order to grasp tissue between jaws (410, 412).

Lower jaw (412) and upper jaw (410) further define a knife pathway (492) that is dimensioned to slidably receive knife member (176) when jaws (410, 412) are in a closed configuration in accordance with the description herein (e.g., as described above with reference to FIGS. 5B-5C).

As best seen in FIG. 9, lower jaw body (482) defines a pair of longitudinally extending recesses (434) and an upwardly extending stud (487) near distal end (486) of lower jaw body (482). Lower jaw (412) of the present example further includes an electrode assembly (450). As best seen in FIG. 9, electrode assembly (450) includes a pair of compressible members (452), a ceramic body (460), and an electrode body (470). Compressible members (452) are configured to fit in recesses (434) of lower jaw body (482). As described in greater detail below with reference to FIGS. 10-12, compressible members (452) are configured to resiliently urge ceramic body (460) and electrode body (470) upwardly relative to lower jaw body (482); while also deforming to accommodate downward movement of ceramic body (460) and electrode body (470) relative to lower jaw body (482). Compressible members (452) thus provide a "float" for ceramic body (460) and electrode body (470). In some versions, compressible members (452) comprise silicone strips, cylinders, or other structures. In some other versions, compressible members (452) comprise leaf springs, coil springs, or other kinds of resilient members. In some other versions, compressible members (452) comprise bladders that are filled with a gel, liquid, or other substance. In some other versions, compressible members (452) comprise foam. In some other versions, compressible members (452) comprise a thermoplastic elastomer that includes polyamide and polyether backbone blocks, such as PEBAX® by Arkema S.A. of Colombes, France. Alternatively, compressible members (452) may take any other suitable form.

Ceramic body (460) of the present example is configured to fit atop compressible members (452). While ceramic is used to form body (460) in the present example, any other suitable electrically insulative material(s) may be used. Ceramic body (460) includes an upper surface (462), an outer edge (464), and a plurality of teeth (424, 426, 428). This plurality of teeth (424, 426, 428) includes a pair of proximal teeth (424), three pairs of middle teeth (426), and a distal tooth (428). While in the current example, there are four pairs of teeth (424, 426) and a distal tooth (428) longitudinally spaced apart from each other, any suitable number of teeth (424, 426, 428) in any suitable array/pattern may be used as would be apparent to one skilled in the art in view of the teachings herein.

Distal end (466) of ceramic body (460) is pivotably seated on stud (487) at distal end (486) of lower jaw body (482). Distal ends (466, 486) thus maintain contact during operation of end effector (480). As described in greater detail below, the proximal end (468) of ceramic body (460) may pivot toward and away from an upper surface (432) of lower jaw body (482), based on the degree to which compressible members (452) are compressed. The spacing between the proximal end (468) of ceramic body (460) and upper surface (432) of lower jaw body (482) is thus variable due to the presence of compressible members (452) in the present example.

Electrode body (470) of the present example is configured to fit atop ceramic body (460) along upper surface (426). Electrode body (470) may be coupled to ceramic body (460) in any suitable fashion, such as via an adhesive, an interference fit, a snap fit, a latch, etc. Electrode body (470) includes an electrode surface (420) defining a plurality of apertures (422). Similar to electrode surface (194) described above, electrode surface (420) may be coupled with a power source such that the power source may provide RF energy to electrode surface (420). An operator may thus selectively activate electrode surface (420) by pressing activation button (130) in accordance with the description above. Electrode surface (420) of lower jaw (412) may cooperate with electrode surfaces (440, 442) of upper jaw (410) to apply bipolar RF energy to tissue that is captured between electrode surface (420) and electrode surfaces (440, 442).

Each tooth (424, 426, 428) of ceramic body (460) is received in a respective aperture (422) defined by electrode surface (420), such that each tooth (424, 426, 428) passes through its respective aperture (422) and protrudes past electrode surface (420). Since teeth (424, 426, 428) are formed by ceramic body (460) in this example, teeth (424, 426, 428) are electrically insulated from electrode surface (420) while also extending above the electrode surface (420). Therefore, if any tooth (424, 426, 428) comes into contact with electrode surfaces (440, 442) of upper jaw (410), such contact will not result in a short circuit.

In the current example, teeth (424, 426, 428) have different heights relative to electrode surface (420). In particular, proximal teeth (424) and distal tooth (428) are taller than middle teeth (426), such that proximal teeth (424) and distal tooth (428) extend past electrode surface (420) further than middle teeth (426). In addition, distal tooth (428) is taller than proximal teeth (424). In some instances, a height disparity among teeth (424, 426, 428) may be intentional. In some other instances, such height disparity may be the unintentional result of irregularities within tolerance in the manufacturing process. In either case, compressible members (452) may provide consistently appropriate performance by end effector (480) regardless of whether teeth (424, 426, 428) have different heights or are of uniform height.

By way of example only, the configuration of distal tooth (428) may promote use of distal tooth (428) to grip tissue as the tissue is being compressed between jaws (410, 412). In addition, or in the alternative, the configuration of distal tooth (428) may prevent tissue from being "milked" or squeezed distally out from jaws (410, 412) as jaws (410, 412) transition to a closed state to compress the tissue. In addition, or in the alternative, the configuration of distal tooth (428) may allow distal tooth (428) to govern the tissue gap at distal ends (414, 486). For instance, as jaws (410, 412) transition to the closed state, distal tooth (428) may contact electrode surface (442) near distal end (414) and thereby prevent distal end (414) from moving further toward distal end (486), even if the operator continues to further pivot closure trigger (126) toward pistol grip (124) after distal tooth (428) makes initial contact with electrode surface (442).

By way of further example only, the configuration of proximal teeth (424) may allow proximal teeth (424) to firmly grip tissue as knife member (174) is driven through knife pathway (492) as knife member (174) is driven distally while the tissue is being compressed between jaws (410, 412). In other words, with proximal teeth (424) firmly gripping the tissue, there may be little to no risk that knife member (174) will push the tissue distally as knife member (174) is driven distally while the tissue is being compressed between jaws (410, 412). In versions where proximal teeth (424) are configured to be taller than middle teeth (426), this greater height of proximal teeth (424) may increase the likelihood of proximal teeth (424) engaging tissue to a desirable extent near proximal end (468) of ceramic body (460). In scenarios where manufacturing variations provide a gap distance between electrode surfaces (420, 440, 442) that is unacceptable along the length of end effector (480), such deviations may also provide unacceptable distances between proximal teeth (424) and upper jaw (410). Thus, the ability of compressible members (452) to promote a gap distance between electrode surfaces (420, 440, 442) that is acceptable along the length of end effector (480) may also promote a desired distance between proximal teeth (424) and upper jaw (410).

Figure 10:
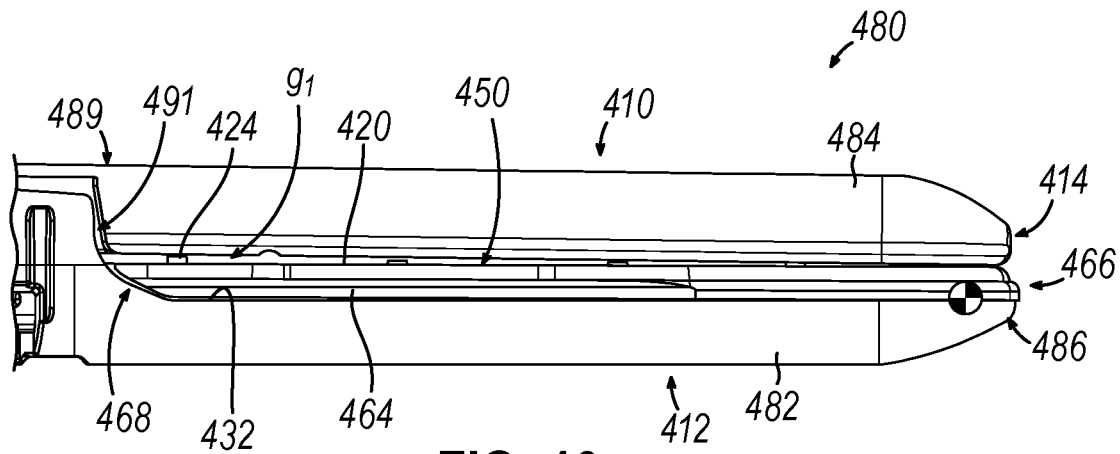
FIG. 10 depicts a side elevation view of a variation of the end effector of FIG. 6, with compressible members omitted, with the end effector in a closed configuration, and with an undesirable gap distance being defined between proximal regions of electrode surfaces of the end effector.

FIG. 10 shows a version of end effector (480) where compressible members (452) are omitted. In this example, manufacturing variations have led to an arrangement where a gap ($g_1$) is left between electrode surfaces (420, 440, 442). This gap ($g_1$) is of an unacceptable magnitude (e.g., greater than approximately 0.006 inches) in this example. Thus, end effector (480) in the state shown in FIG. 10 may not provide suitable tissue sealing when electrode surfaces (420, 440, 442) are activated to apply RF energy. In addition to the distance of gap ($g_1$) between electrode surfaces (420, 440, 442) being unacceptable, proximal teeth (424) are spaced too far away from upper jaw (410) while upper jaw (410) is in the closed position in this example. Thus, end effector (480) in the state shown in FIG. 10 may not provide sufficient grasping of tissue near proximal end (468) of ceramic body (460) while end effector (480) is closed on the tissue.

Figure 11:
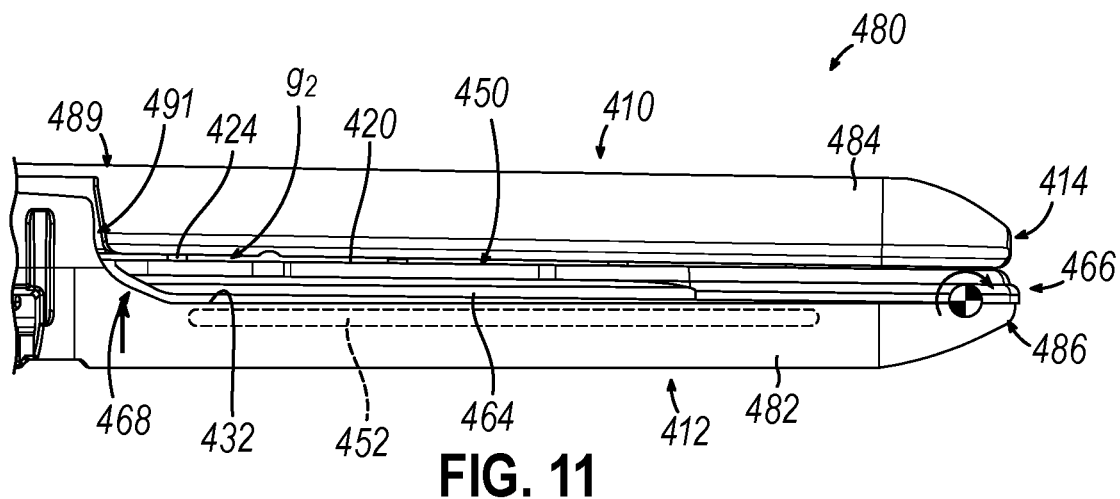
FIG. 11 depicts a side elevation view of the end effector of FIG. 6, with the end effector in a closed configuration, and with compressible members urging a lower electrode assembly upwardly to provide a desirable gap distance between proximal regions of electrode surfaces of the end effector.

FIG. 11 shows how compressible members (452) may address the problems identified above with reference to FIG. 10. As shown in FIG. 11, compressible members (452) resiliently urge proximal end (468) of ceramic body (460) upwardly, such that ceramic body (460) and electrode body (470) pivot clockwise at distal ends (466, 486). Outer edge (464) of ceramic body (460) is spaced away from upper surface (432) of lower jaw body (482). In this configuration, an appropriately sized gap ($g_2$) is defined between electrode surfaces (420, 440, 442). Moreover, proximal teeth (424) are spaced appropriately close to upper jaw (410) (e.g., in contact with upper jaw (410)) while upper jaw (410) is in the closed position in this example. Compressible members (452) thus promote appropriate positioning of electrode surface (420) and proximal teeth (424) despite manufacturing variations that may lead to undesirable results in the absence of compressible members (452).

Figure 12:
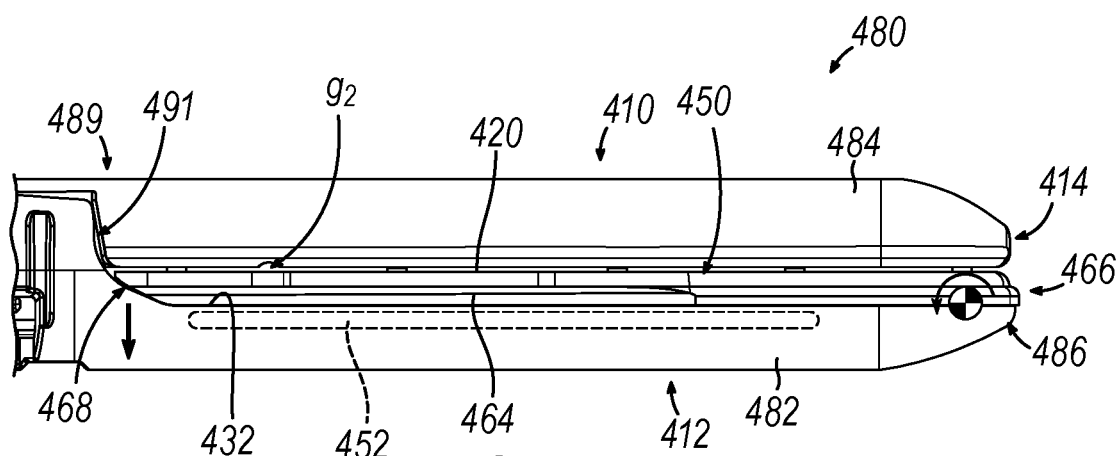
FIG. 12 depicts a side elevation view of the end effector of FIG. 6, with the end effector in a closed configuration, and with compressible members compressing to accommodate downward movement of a lower electrode assembly to provide a desirable gap distance between distal regions of electrode surfaces of the end effector.

FIG. 12 shows another scenario where compressible members (452) may prevent problems that might otherwise occur from manufacturing variations in versions where compressible members (452) are omitted. In this scenario, manufacturing variations have resulted in an arrangement where a proximal portion (489) of upper jaw body (484) is closer to a jaw seat region (491) of lower jaw body (482) than in the arrangement shown in of FIGS. 10-11. In the absence of compressible members (452), the arrangement shown in FIG. 12 may result in a state where upper jaw (410) contacts proximal teeth (424) and/or other structures at the proximal portion of electrode assembly (450) first; which may in turn prevent a suitable degree of contact or distancing at distal ends (414, 466, 486). To avoid such an undesirable result, compressible members (452) compress as shown in FIG. 12 to neutralize the manufacturing variation. In particular, ceramic body (460) and electrode body (470) pivot counterclockwise at distal ends (466, 486), allowing proximal end (468) of ceramic body (460) to travel toward upper surface (432) of lower jaw body (482). The compression of compressible members (452) and corresponding repositioning of ceramic body (460) and electrode body (470) allows end effector (480) to achieve an acceptably sized gap ($g_2$) between electrode surfaces (420, 440, 442) along the length of end effector (480). Similarly, the compression of compressible members (452) and corresponding repositioning of ceramic body (460) and electrode body (470) allows end effector (480) to achieve an acceptably sized positioning of distal tooth (428) in relation to upper jaw (410).

In some scenarios, end effector (480) is assembled with compressible members (452) under ceramic body (460); electrode body (470) is positioned atop ceramic body (460) without yet being fully bonded to ceramic body (460); and then upper jaw (410) is pivoted toward lower jaw (412) to a closed position. In some such scenarios, an adhesive or epoxy is applied between ceramic body (460) and electrode body (470) before this process; and upper jaw (410) is held in the closed position as the adhesive or epoxy cures. In such scenarios, the resilient urging of ceramic body (460) and electrode body (470) toward electrode surfaces (442, 444) may promote fixation of electrode body (470) on ceramic body (460) at a desired vertical position relative to teeth (424, 426, 428) and relative to electrode surfaces (442, 444), despite the manufacturing tolerance issues noted above.

In addition to applying an adhesive or epoxy between ceramic body (460) and electrode body (470) before initial closure of jaws (410, 412) in a manufacturing process, an adhesive or epoxy may also be applied between ceramic body (470) and compressible members (452); between compressible members (452) and lower jaw body (482); and/or between outer edge (464) of ceramic body (460) and upper surface (432) of lower jaw body (482). Adhesive or epoxy may be applied to any one or more of these spaces; and then upper jaw (410) may be pivoted toward lower jaw (412) to reach a closed state. This closed state may be maintained until the adhesive or epoxy cures. During the transition of end effector (480) the open state to the closed state, compressible members (452) may compress and/or bear upon ceramic body (460) and electrode body (470) as described above to ensure that ceramic body (460) and electrode body (470) are appropriately positioned, to thereby ensure that an appropriately sized gap ($g_2$) is defined between electrode surfaces (420, 440, 442). The cured adhesive or epoxy may fix these components in the appropriate position, such that the appropriately sized gap ($g_2$) may continue to be defined between electrode surfaces (420, 440, 442) during subsequent use of end effector (480) in a surgical procedure. Thus, compressible members (452) and the adhesive or epoxy may cooperate during a manufacturing process to establish and then maintain appropriate relative positioning of electrode surfaces (420, 440, 442) despite any tolerance-related inconsistencies occurring with respect to other components of electrosurgical instrument (100).

In addition to, or as an alternative to, using compressible members (452) to neutralize manufacturing variations in end effector (480), a variation of end effector (480) may include a floating hinge pin. FIGS. 13-14 show an example of such a variation. As shown in FIGS. 13-14, an end effector (580) includes an upper jaw (510) and a lower jaw (512). Upper jaw (510) includes an upper jaw body (584) having a proximal portion (589). Lower jaw (512) includes a lower jaw body (582) defining an elongate aperture 583 and an upper surface (532). Lower jaw (512) further includes an electrode assembly (550) that includes compressible members (552). An outer edge (564) of a ceramic body of electrode assembly (550) can be seen between jaw bodies (582, 584). Electrode surfaces are included on upper jaw (510) and electrode assembly (550), respectively. End effector (580) of this example is thus configured and operable just like end effector (480) described above, with the exception that aperture 583 of this example is elongate; whereas the corresponding aperture (497) of end effector (480) is circular.

A pin (514) is disposed in aperture (583) and pivotably couples jaws (510, 512) together. Pin (514) may be configured like pin (415) of end effector (480). Unlike the configuration of end effector (480), pin (514) may translate vertically within aperture (583) as shown in FIGS. 13-14. Such vertical translation of pin (514) within aperture (583) may further promote appropriate positioning of electrode surfaces of jaws (510, 512), thereby further promoting an appropriate gap distance between electrode surfaces of jaws (510, 512). Similarly, vertical translation of pin (514) within aperture (583) may further promote appropriate positioning of teeth of electrode assembly (550) relative to upper jaw (510).

In some scenarios, pin (514) is allowed to "float" vertically within aperture (583) during the manufacturing process. For instance, end effector (580) may be driven to the closed state shown in FIGS. 13-14 during a manufacturing process. During this transition to the closed state, or after reaching the closed state, the proximal portion (589) of upper jaw (510) may be urged downwardly toward lower jaw (582), thereby urging the proximal end (568) of electrode assembly (550) toward jaw seat region (591) of lower jaw body (582). In some scenarios, compressible members (552) of electrode assembly (550) may compress as the proximal portion (589) of upper jaw (510) is urged downwardly toward lower jaw (582). Once the proximal portion (589) of upper jaw (510) reaches the desired vertical position in relation to lower jaw (582), pin (514) may be welded to lower jaw body (582) or otherwise secured to lower jaw body (582), such that pin (514) may no longer "float" vertically within aperture (583). The vertical position of pin (514) may thus be adjusted then fixated during the manufacturing process. Thereafter, the vertical position of pin (514) in aperture (583) may remain constant during normal operation of end effector (580). The degree to which pin (514) may need to move vertically within aperture (583) during the manufacturing process may vary based on the nature and degree of manufacturing variations in the components of end effector (580) that affect the spatial relationship between the proximal end (568) of electrode assembly (550) and jaw seat region (591) of lower jaw body (582). In any case, the adjustment and fixation of the vertical position of pin (514) in aperture (583) during the manufacturing process may ultimately promote appropriate spacing between components of jaws (582, 584) despite such manufacturing variations.

While compressible members (452, 552) are positioned in lower jaws (412, 512) in the examples provided above, compressible members (452, 552) may alternatively be positioned in upper jaws (410, 510). In such versions, upper jaws (410, 510) may also provide a pivotal coupling for electrodes (442, 440) at distal end (414), similar to the pivotal coupling provided via stud (487) near distal end (486) of lower jaw body (482). Alternatively, one set of compressible members (452, 552) may be positioned in upper jaws (410, 510) while another set of compressible members (452, 552) are positioned in lower jaws (412, 512), with each jaw (410, 510, 412, 512) providing a pivotal coupling to the corresponding electrodes at the corresponding distal ends. Upper jaws (410, 510) and lower jaws (412, 512) may thus both have "floating" electrode configurations. Moreover, ceramic bodies (460) may be positioned in upper jaws (410, 510) and lower jaws (412, 512) in an offset fashion. In addition to providing "floating" electrode configurations, compressible members (452, 552) and corresponding ceramic bodies (460) may provide isolation of the thermal mass of the upper and lower electrodes (420, 440, 442) from the bulk mass of the jaw bodies (482, 484, 582, 584).

As yet another example of a variation, end effector (480) may be modified such that compressible members (452, 552) are omitted, with the rest of electrode assembly (450, 550) still being capable of pivoting relative to lower jaw body (482, 582) at the distal end of electrode assembly (450, 550). In such versions, an opening may be formed through lower jaw body (482, 582) near the proximal end of electrode assembly (450, 550). This opening may be configured to receive a pin or other tool that may be used to urge the proximal end of electrode assembly (450, 550) upwardly, thereby pivoting the proximal end of electrode assembly (450, 550) about the distal end of electrode assembly (450, 550) relative to lower jaw body (482, 582). Such pivotal movement may be applied during a manufacturing process as described above. For instance, an adhesive or epoxy may be applied in lower jaw body (482, 582) before electrode assembly (450, 550) is seated in lower jaw body (482, 582). Next, electrode assembly (450, 550) may be placed atop the adhesive or epoxy in lower jaw body (482, 582), and upper jaw (410, 510) may be pivoted toward lower jaw (412, 512) to thereby close end effector (480, 580). Before the adhesive or epoxy cures, the pin or other tool may be used to urge the proximal end of electrode assembly (450, 550) upwardly, thereby pivoting the proximal end of electrode assembly (450, 550) about the distal end of electrode assembly (450, 550) relative to lower jaw body (482, 582) while end effector (480, 580) remains in the closed state. Such pivotal movement of electrode assembly (450, 550) may mimic the upward bias imposed by compressible members (452, 552) as described above, such that the pivotal movement of electrode assembly (450, 550) may establish the appropriate positioning and alignment of electrodes. The adhesive or epoxy may cure with electrode assembly (450, 550) in the appropriately pivoted position, thereby fixing the appropriate positioning and alignment of electrodes.

III. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft assembly having a distal end; and (b) an end effector at the distal end of the shaft assembly, the end effector including: (i) a first jaw, the first jaw including: (A) a first jaw body, and (B) a first electrode surface secured relative to the first jaw body, and (ii) a second jaw pivotably coupled with the first jaw, the second jaw including: (A) a second jaw body having a distal end, and (B) an electrode assembly coupled with the second jaw body, the electrode assembly including: (1) a distal end pivotably supported by the distal end of the second jaw body, (2) a second electrode surface positioned to face the first electrode surface when the first and second jaws are placed in a closed configuration, the first and second electrode surfaces being operable to apply RF energy to tissue, and (3) at least one compressible member interposed between the second electrode surface and the second jaw body, the at least one compressible member being configured to urge a proximal region of the second electrode surface toward a corresponding proximal region of the first electrode surface.

Example 2

The apparatus of Example 1, the distal end of the second jaw body including a protrusion, the protrusion pivotably supporting the distal end of the electrode assembly.

Example 3

The apparatus of Example 2, the protrusion comprising a stud.

Example 4

The apparatus of any of Examples 1 through 3, the electrode assembly further comprising a plurality of teeth, the teeth being positioned to extend toward the first electrode surface when the first and second jaws are placed in a closed configuration.

Example 5

The apparatus of Example 4, the second electrode surface defining a plurality of apertures, the teeth extending through the apertures.

Example 6

The apparatus of any of Examples 4 through 5, the teeth comprising a ceramic material.

Example 7

The apparatus of Example 6, the electrode assembly further comprising a ceramic body, the second electrode surface being positioned on the ceramic body, the ceramic body defining the teeth.

Example 8

The apparatus of Example 7, the ceramic body being interposed between the second electrode surface and the at least one compressible member.

Example 9

The apparatus of any of Examples 4 through 8, the plurality of teeth including at least one proximal tooth, at least one middle tooth, and at least one distal tooth, the at least one proximal tooth, at least one middle tooth, and at least one distal tooth being spaced apart from each other along a length of the second jaw.

Example 10

The apparatus of Example 9, the at least one proximal tooth being taller than the at least one middle tooth.

Example 11

The apparatus of Example 9, the at least one distal tooth being taller than the at least one middle tooth.

Example 12

The apparatus of Example 11, the at least one distal tooth being taller than the at least one proximal tooth.

Example 13

The apparatus of Example 12, the at least one proximal tooth being taller than the at least one middle tooth.

Example 14

The apparatus of any of Examples 1 through 13, the first jaw further defining a first knife pathway, the second jaw further defining a second knife pathway, the first and second knife pathways together being configured to accommodate translation of a knife member through a portion of the end effector.

Example 15

The apparatus of Example 14, the at least one compressible member comprising a first compressible member and a second compressible member, the first compressible member being positioned at a first lateral side of the second knife pathway, the second compressible member being positioned at a second lateral side of the second knife pathway.

Example 16

The apparatus of Example 15, the second jaw body further including: (1) a first recess positioned at the first lateral side of the second knife pathway, the first compressible member being disposed in the first recess, and (2) a second recess positioned at the second lateral side of the second knife pathway, the second compressible member being disposed in the second recess.

Example 17

The apparatus of any of Examples 1 through 16, the at least one compressible member comprising silicone.

Example 18

The apparatus of Example 17, the at least one compressible member comprising a silicone cylinder.

Example 19

An apparatus, comprising: (a) a shaft assembly having a distal end; and (b) an end effector at the distal end of the shaft assembly, the end effector including: (i) a first jaw, the first jaw including: (A) a first jaw body, and (B) a first electrode surface secured relative to the first jaw body, and (ii) a second jaw pivotably coupled with the first jaw, the second jaw including: (A) a second jaw body having a distal end, and (B) an electrode assembly coupled with the second jaw body, the electrode assembly including: (1) an electrically insulative body having a distal end pivotably supported by the distal end of the second jaw body, (2) a second electrode surface secured relative to the electrically insulative body, the first and second electrode surfaces being operable to apply RF energy to tissue, and (3) at least one compressible member interposed between the second electrode surface and the second jaw body, the at least one compressible member being configured to urge a proximal region of the second electrode surface toward a corresponding proximal region of the first electrode surface.

Example 20

An apparatus, comprising: (a) a shaft assembly having a distal end; and (b) an end effector at the distal end of the shaft assembly, the end effector including: (i) a first jaw, the first jaw including: (A) a first jaw body, and (B) a first electrode surface secured relative to the first jaw body, (ii) a second jaw pivotably coupled with the first jaw, the second jaw including: (A) a second jaw body, and (B) an electrode assembly coupled with the second jaw body, the electrode assembly including: (1) a second electrode surface, the first and second electrode surfaces being operable to apply RF energy to tissue, and (2) at least one compressible member interposed between the second electrode surface and the second jaw body, the at least one compressible member being configured to urge a proximal region of the second electrode surface toward a corresponding proximal region of the first electrode surface, and (iii) a knife member, the knife member being operable to translate through portions of the first and second jaws to sever tissue captured between the first and second jaws.

Example 21

A method of assembling an apparatus, the method comprising: (a) providing an end effector having a first jaw and a second jaw, the end effector being operable to transition between an open state and a closed state; (b) positioning an adhesive or epoxy in the second jaw; (c) positioning an electrode assembly in the second jaw, the electrode assembly contacting the adhesive or epoxy in the second jaw, the electrode assembly having a distal end pivotally engaging a distal end of the second jaw; (d) transitioning the end effector from the open state to the closed state, thereby bringing a portion of the first jaw into contact with a portion of the electrode assembly; (e) pivoting a proximal end of the electrode assembly relative to the distal end of the electrode assembly while the end effector remains in the closed state, thereby establishing a predetermined alignment between the electrode assembly and a corresponding region of the first jaw; and (f) maintaining the end effector in the closed state until the adhesive or epoxy cures.

Example 22

The method of claim 21, further comprising positioning a compressible member between the electrode assembly and the lower jaw, the compressible member providing the pivoting of the proximal end of the electrode assembly relative to the distal end of the electrode assembly while the end effector remains in the closed state.

Example 23

The method of claim 21, the act of pivoting the proximal end of the electrode assembly relative to the distal end of the electrode assembly comprising manipulating a tool to push the proximal end of the electrode assembly.

Example 24

The method of claim 21, the first jaw and the second jaw being pivotally coupled together via a pivot pin in an elongate slot, the method further comprising moving the pivot pin within the elongate slot from a first pin position to a second pin position after transitioning the end effector from the open state to the closed state, while maintaining the end effector in the closed state, to thereby establish a predetermined alignment between the first jaw and the second jaw.

Example 25

The method of claim 24, further comprising welding the pivot pin in the second pin position after moving the pivot pin within the elongate slot from the first pin position to the second pin position.

IV. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those of ordinary skill in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein, in its entirety.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a shaft assembly having a distal end; and
   (b) an end effector at the distal end of the shaft assembly, the end effector including:
      (i) a first jaw, the first jaw including:
         (A) a first jaw body, and
         (B) a first electrode surface secured relative to the first jaw body, and
      (ii) a second jaw pivotably coupled with the first jaw, the second jaw including:
         (A) a second jaw body having a distal end, and
         (B) an electrode assembly coupled with the second jaw body, the electrode assembly including:
            (1) a distal end pivotably supported by the distal end of the second jaw body,
            (2) a second electrode surface positioned to face the first electrode surface when the first and second jaws are placed in a closed configuration, the first and second electrode surfaces being operable to apply RF energy to tissue, and
            (3) at least one compressible member interposed between the second electrode surface and the second jaw body, the at least one compressible member being configured to urge a proximal region of the second electrode surface toward a corresponding proximal region of the first electrode surface.

2. The apparatus of claim 1, the distal end of the second jaw body including a protrusion, the protrusion pivotably supporting the distal end of the electrode assembly.

3. The apparatus of claim 1, the electrode assembly further comprising a plurality of teeth, the teeth being positioned to extend toward the first electrode surface when the first and second jaws are placed in a closed configuration.

4. The apparatus of claim 3, the second electrode surface defining a plurality of apertures, the teeth extending through the apertures.

5. The apparatus of claim 3, the teeth comprising a ceramic material.

6. The apparatus of claim 5, the electrode assembly further comprising a ceramic body, the second electrode surface being positioned on the ceramic body, the ceramic body defining the teeth.

7. The apparatus of claim 6, the ceramic body being interposed between the second electrode surface and the at least one compressible member.

8. The apparatus of claim 3, the plurality of teeth including at least one proximal tooth, at least one middle tooth, and at least one distal tooth, the at least one proximal tooth, at least one middle tooth, and at least one distal tooth being spaced apart from each other along a length of the second jaw.

9. The apparatus of claim 8, the at least one proximal tooth being taller than the at least one middle tooth.

10. The apparatus of claim 8, the at least one distal tooth being taller than the at least one middle tooth.

11. The apparatus of claim 10, the at least one distal tooth being taller than the at least one proximal tooth.

12. The apparatus of claim 1, the first jaw further defining a first knife pathway, the second jaw further defining a second knife pathway, the first and second knife pathways together being configured to accommodate translation of a knife member through a portion of the end effector.

13. The apparatus of claim 12, the at least one compressible member comprising a first compressible member and a second compressible member, the first compressible member being positioned at a first lateral side of the second knife pathway, the second compressible member being positioned at a second lateral side of the second knife pathway.

14. The apparatus of claim 1, the at least one compressible member comprising silicone.

15. A method of assembling an apparatus, the method comprising:
   (a) providing an end effector having a first jaw and a second jaw, the end effector being operable to transition between an open state and a closed state;
   (b) positioning an adhesive or epoxy in the second jaw;
   (c) positioning an electrode assembly in the second jaw, the electrode assembly contacting the adhesive or epoxy in the second jaw, the electrode assembly having a distal end pivotally engaging a distal end of the second jaw;
   (d) transitioning the end effector from the open state to the closed state, thereby bringing a portion of the first jaw into contact with a portion of the electrode assembly;
   (e) pivoting a proximal end of the electrode assembly relative to the distal end of the electrode assembly while the end effector remains in the closed state, thereby establishing a predetermined alignment between the electrode assembly and a corresponding region of the first jaw; and
   (f) maintaining the end effector in the closed state until the adhesive or epoxy cures.

16. The method of claim 15, further comprising positioning a compressible member between the electrode assembly and the lower jaw, the compressible member providing the pivoting of the proximal end of the electrode assembly relative to the distal end of the electrode assembly while the end effector remains in the closed state.

17. The method of claim 15, the act of pivoting the proximal end of the electrode assembly relative to the distal end of the electrode assembly comprising manipulating a tool to push the proximal end of the electrode assembly.

18. The method of claim 15, the first jaw and the second jaw being pivotally coupled together via a pivot pin in an elongate slot, the method further comprising moving the pivot pin within the elongate slot from a first pin position to a second pin position after transitioning the end effector from the open state to the closed state, while maintaining the end effector in the closed state, to thereby establish a predetermined alignment between the first jaw and the second jaw.

19. The method of claim 18, further comprising welding the pivot pin in the second pin position after moving the pivot pin within the elongate slot from the first pin position to the second pin position.

20. An apparatus, comprising:
(a) a shaft assembly having a distal end; and
(b) an end effector at the distal end of the shaft assembly, the end effector including:
  (i) a first jaw, the first jaw including:
    (A) a first jaw body, and
    (B) a first electrode surface secured relative to the first jaw body, and
  (ii) a second jaw pivotably coupled with the first jaw, the second jaw including:
    (A) a second jaw body having a distal end, and
    (B) an electrode assembly coupled with the second jaw body, the electrode assembly including:
      (1) an electrically insulative body having a distal end pivotably supported by the distal end of the second jaw body,
      (2) a second electrode surface secured relative to the electrically insulative body, the first and second electrode surfaces being operable to apply RF energy to tissue, and
      (3) at least one compressible member interposed between the second electrode surface and the second jaw body, the at least one compressible member being configured to urge a proximal region of the second electrode surface toward a corresponding proximal region of the first electrode surface.

* * * * *